(12) United States Patent
Schultheis et al.

(10) Patent No.: US 12,708,442 B2
(45) Date of Patent: Aug. 18, 2026

(54) ELECTRICAL ANALYZER ASSEMBLY FOR INTRAVASCULAR LITHOTRIPSY DEVICE

(71) Applicant: Boston Scientific Scimed, Inc., Maple Grove, MN (US)

(72) Inventors: Eric Schultheis, San Clemente, CA (US); Gerald D. Bacher, Carlsbad, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 513 days.

(21) Appl. No.: 18/139,624

(22) Filed: Apr. 26, 2023

(65) Prior Publication Data

US 2023/0255688 A1 Aug. 17, 2023

Related U.S. Application Data

(63) Continuation of application No. 17/211,150, filed on Mar. 24, 2021, now Pat. No. 11,707,323.

(Continued)

(51) Int. Cl.

*A61B 18/24* (2006.01)
*A61B 17/00* (2006.01)
*A61B 18/00* (2006.01)

(52) U.S. Cl.

CPC .. *A61B 18/245* (2013.01); *A61B 2017/00026* (2013.01); *A61B 2017/00039* (2013.01);

(Continued)

(58) Field of Classification Search

CPC ........ A61B 18/245; A61B 2017/00026; A61B 2017/00039; A61B 2017/00154; A61B 2018/0022

See application file for complete search history.

(56) References Cited

U.S. PATENT DOCUMENTS 4,649,924 A 3/1987 Taccardi
4,699,147 A 10/1987 Chilson et al.

(Continued)

FOREIGN PATENT DOCUMENTS

AU 2017205323 7/2017
AU 2022227829 9/2022

(Continued)

OTHER PUBLICATIONS

Definition of ablation—NCI Dictionary of Cancer Terms—NCI, National Cancer Institute, p. 1 (Year:2025).

(Continued)

*Primary Examiner* — Carl H Layno
*Assistant Examiner* — Aya Ziad Bakkar
(74) *Attorney, Agent, or Firm* — SEAGER, TUFTE & WICKHEM, LLP

(57) ABSTRACT

A method for treating a treatment site within or adjacent to a vessel wall or heart valve within a body of a patient includes the steps of generating energy with an energy source; positioning a balloon substantially adjacent to the treatment site, the balloon having a balloon wall that defines a balloon interior that receives a balloon fluid; receiving energy from the energy source with an energy guide; guiding the energy with the energy guide into the balloon interior; monitoring a condition of the balloon with an electrical analyzer assembly while energy is being guided into the balloon interior, the electrical analyzer assembly including (i) a first electrode, (ii) a second electrode that is in fluid communication with blood of the patient, and (iii) an impedance detector that is electrically coupled to the first electrode and the second electrode; and detecting an impedance between the first electrode and the second electrode with the impedance detector.

20 Claims, 6 Drawing Sheets

Related U.S. Application Data

(60) Provisional application No. 63/004,977, filed on Apr. 3, 2020.

(52) U.S. Cl.
CPC .............. *A61B 2017/00154* (2013.01); *A61B 2018/0022* (2013.01)

(56) References Cited

U.S. PATENT DOCUMENTS 4,799,479 A 1/1989 Spears
4,850,351 A 7/1989 Herman
4,913,142 A 4/1990 Kittrell et al.
4,932,954 A 6/1990 Wondrazek et al.
4,955,895 A 9/1990 Suglyama
4,960,108 A 10/1990 Reichel et al.
4,994,059 A 2/1991 Kosa et al.
4,998,930 A 3/1991 Lundahl
5,019,075 A 5/1991 Spears et al.
5,034,010 A 7/1991 Kittrell et al.
5,041,121 A 8/1991 Wondrazek et al.
5,057,106 A 10/1991 Kasevich et al.
5,082,343 A 1/1992 Coult et al.
5,093,877 A 3/1992 Aita et al.
5,104,391 A 4/1992 Ingle
5,104,392 A 4/1992 Kittrell et al.
5,109,452 A 4/1992 Selvin et al.
5,116,227 A 5/1992 Levy
5,126,165 A 6/1992 Akihama et al.
5,152,768 A 10/1992 Bhatta
5,173,049 A 12/1992 Levy
5,176,674 A 1/1993 Hofmann
5,181,921 A 1/1993 Makita et al.
5,188,632 A 2/1993 Goldenberg
5,200,838 A 4/1993 Nudelman
5,269,777 A 12/1993 Doiron
5,290,277 A 3/1994 Vercimak et al.
5,324,282 A 6/1994 Dodick
5,328,472 A 7/1994 Steinke et al.
5,336,184 A 8/1994 Teirstein
5,363,458 A 11/1994 Pan
5,372,138 A 12/1994 Crowley
5,387,225 A 2/1995 Euteneur
5,400,428 A 3/1995 Grace
5,410,797 A 5/1995 Steinke et al.
5,417,689 A 5/1995 Fine
5,422,926 A 6/1995 Smith
5,431,647 A 7/1995 Purcell
5,454,809 A 10/1995 Janssen
5,456,680 A 10/1995 Taylor
5,474,537 A 12/1995 Solar
5,496,311 A 3/1996 Abele et al.
5,509,917 A 4/1996 Cecchetti
5,519,798 A 5/1996 Shahid
5,540,679 A 7/1996 Fram
5,562,657 A 10/1996 Griffin
5,598,494 A 1/1997 Behrmann et al.
5,609,606 A 3/1997 O'Boyle
5,611,807 A 3/1997 O'Boyle
5,637,877 A 6/1997 Sinofsky
5,661,829 A 8/1997 Zheng
5,697,377 A 12/1997 Wittkamph
5,718,241 A 2/1998 Ben-Haim et al.
5,729,583 A 3/1998 Tang
5,764,843 A 6/1998 Macken et al.
5,772,609 A 6/1998 Nguyen et al.
5,860,974 A 1/1999 Abele
5,891,135 A 4/1999 Jackson et al.
5,906,611 A 5/1999 Dodick et al.
5,944,697 A 8/1999 Benett et al.
6,007,514 A 12/1999 Nita
6,015,404 A 1/2000 Altshuler
6,080,119 A 6/2000 Schwarze et al.
6,123,923 A 9/2000 Unger
6,139,510 A 10/2000 Palermo
6,186,963 B1 2/2001 Schwarze et al.
6,203,537 B1 3/2001 Adrian
6,210,404 B1 4/2001 Shadduck
6,339,470 B1 1/2002 Papademetriou et al.
6,356,575 B1 3/2002 Fukumoto
6,368,318 B1 4/2002 Visuri et al.
6,423,055 B1 7/2002 Farr
6,500,174 B1 12/2002 Maguire et al.
6,514,203 B2 2/2003 Bukshpan
6,514,249 B1 2/2003 Maguire
6,524,251 B2 2/2003 Rabiner et al.
6,538,739 B1 3/2003 Visuri et al.
6,544,218 B1 4/2003 Choi
6,548,010 B1 4/2003 Stivland et al.
6,560,387 B1 5/2003 Hehlen et al.
6,607,502 B1 8/2003 Maguire et al.
6,631,220 B1 10/2003 Liang et al.
6,652,547 B2 11/2003 Rabiner et al.
6,666,834 B2 12/2003 Restle et al.
6,702,781 B1 3/2004 Reifart et al.
6,773,447 B2 8/2004 Laguna
6,824,554 B1 11/2004 Jang
6,849,994 B1 2/2005 White et al.
6,890,317 B2 5/2005 Gerdts et al.
6,947,785 B1 9/2005 Beatty et al.
6,966,890 B2 11/2005 Coyle et al.
6,978,168 B2 12/2005 Beatty et al.
6,990,370 B1 1/2006 Beatty et al.
7,273,470 B2 9/2007 Wantink
7,309,324 B2 12/2007 Hayes et al.
7,367,967 B2 5/2008 Eidenschink
7,470,240 B2 12/2008 Schultheiss et al.
7,539,231 B1 5/2009 Honea et al.
7,569,032 B2 8/2009 Naimark et al.
7,599,588 B2 10/2009 Eberle et al.
7,641,646 B2 1/2010 Kennedy, II
7,691,079 B2 4/2010 Gobel
7,713,260 B2 5/2010 Lessard
7,758,572 B2 7/2010 Weber et al.
7,762,984 B2 7/2010 Kumoyama et al.
7,810,395 B2 10/2010 Zhou
7,850,685 B2 12/2010 Kunis et al.
7,867,178 B2 1/2011 Simnacher
7,909,797 B2 3/2011 Kennedy, II et al.
7,942,850 B2 5/2011 Levit et al.
7,967,781 B2 6/2011 Simpson et al.
7,972,299 B2 7/2011 Carter
7,985,189 B1 7/2011 Ogden et al.
8,021,328 B2 9/2011 Lee
8,029,473 B2 10/2011 Carter
8,043,256 B2 10/2011 Hansen
8,066,732 B2 11/2011 Paul et al.
8,088,121 B2 1/2012 Nishide
8,157,760 B2 4/2012 Criado et al.
8,162,859 B2 4/2012 Schultheiss et al.
8,166,825 B2 5/2012 Zhou
8,192,368 B2 6/2012 Woodruff
8,197,505 B2 6/2012 Hirszowicz et al.
8,246,643 B2 8/2012 Nita
8,267,886 B2 9/2012 Ewing
8,292,913 B2 10/2012 Warnack
8,328,820 B2 12/2012 Diamant
8,364,235 B2 1/2013 Kordis et al.
8,372,034 B2 2/2013 Levit
8,382,738 B2 2/2013 Simpson et al.
8,414,527 B2 4/2013 Mallaby
8,419,613 B2 4/2013 Saadat
8,439,890 B2 5/2013 Beyar
8,556,813 B2 10/2013 Cashman et al.
8,556,851 B2 10/2013 Hirszowicz
8,574,247 B2 11/2013 Adams et al.
8,657,814 B2 2/2014 Werneth
8,709,075 B2 4/2014 Adams et al.
8,728,091 B2 5/2014 Hakala et al.
8,734,424 B2 5/2014 Watanabe
8,747,416 B2 6/2014 Hakala et al.
8,784,362 B2 7/2014 Boutilette
8,834,510 B2 9/2014 Wilson et al.
8,888,788 B2 11/2014 Hakala et al.

(56) References Cited

U.S. PATENT DOCUMENTS 8,956,371 B2 2/2015 Hawkins et al.
8,956,374 B2 2/2015 Hawkins et al.
8,986,339 B2 3/2015 Warnack
8,992,519 B2 3/2015 Kim et al.
8,992,817 B2 3/2015 Stamberg
9,005,216 B2 4/2015 Hakala et al.
9,011,462 B2 4/2015 Adams et al.
9,011,463 B2 4/2015 Adams et al.
9,011,511 B2 4/2015 Gregorich
9,044,575 B2 6/2015 Beasley et al.
9,044,618 B2 6/2015 Hawkins et al.
9,044,619 B2 6/2015 Hawkins et al.
9,056,185 B2 6/2015 Fischell et al.
9,072,534 B2 7/2015 Adams et al.
9,089,669 B2 7/2015 Haslinger et al.
9,131,949 B2 9/2015 Coleman et al.
9,138,249 B2 9/2015 Adams et al.
9,138,260 B2 9/2015 Miller et al.
9,180,280 B2 11/2015 Hawkins et al.
9,220,521 B2 12/2015 Hawkins et al.
9,237,984 B2 1/2016 Hawkins et al.
9,254,169 B2 2/2016 Long et al.
9,282,984 B2 3/2016 Nita
9,283,359 B2 3/2016 Pepper
9,289,132 B2 3/2016 Ghaffari et al.
9,289,224 B2 3/2016 Adams et al.
9,289,319 B2 3/2016 Pacetti et al.
9,320,530 B2 4/2016 Grace
9,333,000 B2 5/2016 Hakala et al.
9,339,632 B2 5/2016 Eidenschink et al.
9,364,645 B2 6/2016 Erikawa
9,375,223 B2 6/2016 Wallace
9,421,025 B2 8/2016 Hawkins et al.
9,433,428 B2 9/2016 Hakala et al.
9,433,745 B2 9/2016 Cully
9,504,809 B2 11/2016 Bo
9,510,887 B2 12/2016 Burnett
9,522,012 B2 12/2016 Adams
9,554,815 B2 1/2017 Adams et al.
9,555,267 B2 1/2017 Ein-gal
9,566,209 B2 2/2017 Katragadda et al.
9,579,114 B2 2/2017 Mantell et al.
9,579,492 B2 2/2017 Simpson
9,585,684 B2 3/2017 Nita et al.
9,592,328 B2 3/2017 Jeevanandam
9,603,506 B2 3/2017 Goldfarb et al.
9,629,567 B2 4/2017 Porath et al.
9,642,673 B2 5/2017 Adams
9,662,069 B2 5/2017 De Graff et al.
9,687,166 B2 6/2017 Subramaniam
9,700,655 B2 7/2017 Laudenslager et al.
9,730,715 B2 8/2017 Adams
9,737,361 B2 8/2017 Magana
9,764,142 B2 9/2017 Imran
9,782,570 B2 10/2017 Hirszowicz
9,814,476 B2 11/2017 Adams et al.
9,833,348 B2 12/2017 Jordan et al.
9,839,764 B2 12/2017 Chouinard
9,861,377 B2 1/2018 Mantell et al.
9,867,629 B2 1/2018 Hawkins et al.
9,878,135 B2 1/2018 Holzapfel et al.
9,894,756 B2 2/2018 Weinkam et al.
9,901,704 B2 2/2018 Appling
9,955,946 B2 5/2018 Miller et al.
9,974,963 B2 5/2018 Imran
9,974,970 B2 5/2018 Nuta et al.
9,993,292 B2 6/2018 Adams et al.
10,039,561 B2 8/2018 Adams et al.
10,076,384 B2 9/2018 Kasprzyk
10,086,175 B2 10/2018 Torres et al.
10,124,153 B2 11/2018 Feig
10,136,829 B2 11/2018 Deno et al.
10,149,690 B2 12/2018 Hawkins et al.
10,159,505 B2 12/2018 Hakala et al.
10,194,994 B2 2/2019 Deno et al.
10,201,387 B2 2/2019 Grace et al.
10,206,698 B2 2/2019 Hakala et al.
10,226,265 B2 3/2019 Ku et al.
10,245,410 B2 4/2019 Aggerholm
10,327,846 B1 6/2019 Stark et al.
10,328,290 B2 6/2019 Zhou et al.
10,357,264 B2 7/2019 Kat-Kuoy
10,405,923 B2 9/2019 Yu et al.
10,406,031 B2 9/2019 Thyzel
10,406,318 B2 9/2019 Williams
10,420,569 B2 9/2019 Adams
10,439,791 B2 10/2019 Kalhan
10,441,300 B2 10/2019 Hawkins
10,449,339 B2 10/2019 Wilson et al.
10,463,430 B2 11/2019 Dick
10,478,202 B2 11/2019 Adams et al.
10,517,620 B2 12/2019 Adams
10,517,621 B1 12/2019 Hakala et al.
10,537,287 B2 1/2020 Braido et al.
10,555,744 B2 2/2020 Nguyen et al.
10,561,428 B2 2/2020 Eggert et al.
10,583,277 B2 3/2020 Rundquist
10,589,073 B2 3/2020 Mallaby
10,617,850 B2 4/2020 Tal
10,646,240 B2 5/2020 Betelia et al.
10,668,245 B2 6/2020 Kanae
10,682,178 B2 6/2020 Adams et al.
10,695,531 B2 6/2020 Suzuki
10,702,293 B2 7/2020 Adams et al.
10,709,462 B2 7/2020 Nguyen et al.
10,709,872 B2 7/2020 Alvarez et al.
10,758,255 B2 9/2020 Adams
10,797,684 B1 10/2020 Benz et al.
10,799,688 B2 10/2020 Calhoun
10,842,567 B2 11/2020 Grace et al.
10,850,075 B2 12/2020 Tarunaga
10,857,329 B2 12/2020 Davies
10,933,225 B2 3/2021 Campbell
10,952,740 B2 3/2021 Dasnurkar et al.
10,952,790 B2 3/2021 Haverkost et al.
10,959,743 B2 3/2021 Adams et al.
10,966,737 B2 4/2021 Nguyen
10,967,156 B2 4/2021 Gulachenski
10,973,538 B2 4/2021 Hakala et al.
10,974,028 B2 4/2021 Buller et al.
10,980,987 B2 4/2021 Tarunaga
11,000,299 B2 5/2021 Hawkins et al.
11,020,135 B1 6/2021 Hawkins
11,026,707 B2 6/2021 Ku et al.
11,040,176 B2 6/2021 Blanchard et al.
11,058,492 B2 7/2021 Grace et al.
11,076,874 B2 8/2021 Hakala et al.
11,116,939 B2 9/2021 Jamous et al.
11,141,131 B2 10/2021 Stigall
11,179,169 B2 11/2021 Brouillete et al.
11,207,493 B2 12/2021 Suzuki et al.
11,213,661 B2 1/2022 Spindler
11,229,772 B2 1/2022 Nita
11,229,776 B2 1/2022 Kugler et al.
11,246,659 B2 2/2022 Grace et al.
11,253,681 B2 2/2022 Williams
11,266,817 B2 3/2022 Cope et al.
11,389,171 B2 7/2022 Goldsmith
11,389,628 B2 7/2022 Spencer
11,395,669 B2 7/2022 O'Malley et al.
11,399,862 B2 8/2022 Massimini et al.
11,406,452 B2 8/2022 Efremkin
11,406,799 B2 8/2022 McEvaddy et al.
11,484,327 B2 11/2022 Anderson et al.
11,540,848 B2 1/2023 Cai et al.
11,564,729 B2 1/2023 Walzman
11,602,363 B2 3/2023 Nguyen
11,633,200 B2 4/2023 Anderson et al.
11,672,585 B2 6/2023 Schultheis
11,672,599 B2 6/2023 Schultheis et al.
11,707,323 B2 7/2023 Schultheis et al.
11,771,449 B2 10/2023 Adams et al.
11,779,363 B2 10/2023 Vo
11,826,530 B2 11/2023 Suzuki

(56) References Cited

U.S. PATENT DOCUMENTS 11,839,391 B2 12/2023 Schultheis et al.
11,911,054 B2 2/2024 Singla
11,911,056 B2 2/2024 Anderson et al.
11,918,285 B2 3/2024 Sun et al.
11,944,331 B2 4/2024 Anderson et al.
11,950,793 B2 4/2024 Nguyen
12,011,185 B2 6/2024 Vo
12,023,098 B2 7/2024 Nguyen
12,035,932 B1 7/2024 Nunes
12,076,077 B2 9/2024 Mori
12,144,516 B2 11/2024 Betelia
12,178,458 B1 12/2024 Betelia et al.
12,193,691 B2 1/2025 Adams
2001/0016761 A1 8/2001 Rudie
2001/0018569 A1 8/2001 Erbel
2001/0020164 A1 9/2001 Papademetriou
2001/0049464 A1 12/2001 Ganz
2001/0051784 A1 12/2001 Brisken
2002/0045811 A1 4/2002 Kittrell et al.
2002/0052621 A1 5/2002 Fried et al.
2002/0065512 A1 5/2002 Fjield et al.
2002/0082553 A1 6/2002 Duchamp
2002/0183620 A1 12/2002 Tearney
2002/0183729 A1 12/2002 Farr et al.
2002/0188204 A1 12/2002 McNamara et al.
2003/0009157 A1 1/2003 Levine et al.
2003/0050632 A1 3/2003 Fjield et al.
2003/0065316 A1 4/2003 Levine et al.
2003/0114901 A1 6/2003 Loeb et al.
2003/0125719 A1 7/2003 Furnish
2003/0144654 A1 7/2003 Hilal
2003/0176873 A1 9/2003 Chernenko et al.
2004/0002677 A1 1/2004 Gentsler
2004/0024349 A1 2/2004 Flock et al.
2004/0073251 A1 4/2004 Weber
2004/0097996 A1 5/2004 Rabiner
2004/0133254 A1 7/2004 Sterzer et al.
2004/0162508 A1 8/2004 Uebelacker
2004/0210278 A1 10/2004 Boll
2004/0243119 A1 12/2004 Lane et al.
2004/0249401 A1 12/2004 Rabiner
2004/0254570 A1 12/2004 Hadsjicostis
2005/0010095 A1 1/2005 Stewart et al.
2005/0021013 A1 1/2005 Visuri
2005/0080396 A1 4/2005 Rontal
2005/0113722 A1 5/2005 Schultheiss
2005/0171437 A1 8/2005 Carberry
2005/0171527 A1 8/2005 Bhola
2005/0251131 A1 11/2005 Lesh
2005/0259319 A1 11/2005 Brooker
2005/0273014 A1 12/2005 Gianchandani et al.
2005/0277839 A1 12/2005 Alderman et al.
2006/0033241 A1 2/2006 Schewe et al.
2006/0084966 A1 4/2006 Maguire et al.
2006/0098921 A1 5/2006 Benaron et al.
2006/0142703 A1 6/2006 Carter
2006/0190022 A1 8/2006 Beyar et al.
2006/0200039 A1 9/2006 Brockway et al.
2006/0221528 A1 10/2006 Li et al.
2006/0241524 A1 10/2006 Lee et al.
2006/0241572 A1 10/2006 Zhou
2006/0241733 A1 10/2006 Zhang et al.
2006/0270976 A1 11/2006 Savage et al.
2007/0027524 A1 2/2007 Johnson
2007/0043340 A1 2/2007 Thyzel
2007/0060990 A1 3/2007 Satake
2007/0088380 A1 4/2007 Hirszowicz et al.
2007/0118057 A1 5/2007 Ein-gal
2007/0142779 A1 6/2007 Duane
2007/0142819 A1 6/2007 El-Nounou et al.
2007/0142821 A1 6/2007 Hennessy et al.
2007/0142856 A1 6/2007 Jang
2007/0179496 A1 8/2007 Swoyer
2007/0239082 A1 10/2007 Schultheiss et al.
2007/0255270 A1 11/2007 Carney
2007/0264353 A1 11/2007 Myntti et al.
2007/0270897 A1 11/2007 Skerven
2007/0280311 A1 12/2007 Hofmann
2007/0299392 A1 12/2007 Beyar et al.
2008/0033519 A1 2/2008 Burwell
2008/0081950 A1 4/2008 Koenig et al.
2008/0086118 A1 4/2008 Lai
2008/0095714 A1 4/2008 Castella et al.
2008/0097251 A1 4/2008 Babaev
2008/0108867 A1 5/2008 Zhou
2008/0114341 A1 5/2008 Thyzel
2008/0132810 A1 6/2008 Scoseria et al.
2008/0175539 A1 7/2008 Brown
2008/0195088 A1 8/2008 Farr et al.
2008/0214891 A1 9/2008 Slenker et al.
2008/0221550 A1 9/2008 Lee
2008/0281157 A1 11/2008 Miyagi et al.
2008/0296152 A1 12/2008 Voss
2008/0319356 A1 12/2008 Cain et al.
2009/0036803 A1 2/2009 Warlick et al.
2009/0043300 A1 2/2009 Reitmajer et al.
2009/0054881 A1 2/2009 Krespi
2009/0097806 A1 4/2009 Viellerobe et al.
2009/0125007 A1 5/2009 Splinter
2009/0131921 A1 5/2009 Kurtz et al.
2009/0192495 A1 7/2009 Ostrovsky et al.
2009/0240242 A1 9/2009 Neuberger
2009/0247945 A1 10/2009 Levit
2009/0281531 A1 11/2009 Rizoiu
2009/0292296 A1 11/2009 Pansky
2009/0296751 A1 12/2009 Kewitsch et al.
2009/0299327 A1 12/2009 Tilson et al.
2009/0306533 A1 12/2009 Rousche
2009/0312768 A1 12/2009 Hawkins et al.
2010/0016862 A1 1/2010 Hawkins et al.
2010/0036238 A1 2/2010 Neidert
2010/0036294 A1 2/2010 Mantell et al.
2010/0063491 A1 3/2010 Verhagen
2010/0094209 A1 4/2010 Drasler et al.
2010/0114020 A1 5/2010 Hawkins et al.
2010/0114065 A1 5/2010 Hawkins et al.
2010/0125268 A1 5/2010 Gustus et al.
2010/0160838 A1 6/2010 Krespi
2010/0160903 A1 6/2010 Krespi
2010/0168572 A1 7/2010 Sliwa
2010/0168836 A1 7/2010 Kassab
2010/0168862 A1 7/2010 Edie et al.
2010/0179632 A1 7/2010 Bruszewski et al.
2010/0191089 A1 7/2010 Stebler et al.
2010/0198114 A1 8/2010 Novak et al.
2010/0199773 A1 8/2010 Zhou
2010/0222786 A1 9/2010 Kassab
2010/0234875 A1 9/2010 Allex et al.
2010/0256535 A1 10/2010 Novak et al.
2010/0265733 A1 10/2010 O'Leary
2010/0286791 A1 11/2010 Goldsmith
2010/0316333 A1 12/2010 Luther
2011/0034832 A1 2/2011 Cioanta et al.
2011/0059415 A1 3/2011 Kasenbacher
2011/0082452 A1 4/2011 Melsky
2011/0082534 A1 4/2011 Wallace
2011/0118634 A1 5/2011 Golan
2011/0144502 A1 6/2011 Zhou et al.
2011/0184244 A1 7/2011 Kagaya et al.
2011/0208185 A1 8/2011 Diamant et al.
2011/0213349 A1 9/2011 Brown
2011/0245740 A1 10/2011 Novak et al.
2011/0257641 A1 10/2011 Hastings et al.
2011/0263921 A1 10/2011 Vrba et al.
2011/0275990 A1 11/2011 Besser et al.
2011/0306956 A1 12/2011 Islam
2012/0064141 A1 3/2012 Andreacchi et al.
2012/0071715 A1 3/2012 Beyar et al.
2012/0071867 A1 3/2012 Ryan
2012/0071889 A1 3/2012 Mantell et al.
2012/0089132 A1 4/2012 Dick et al.
2012/0095335 A1 4/2012 Sverdlik et al.
2012/0095461 A1 4/2012 Herscher et al.
2012/0116289 A1 5/2012 Hawkins et al.

(56) References Cited

U.S. PATENT DOCUMENTS

2012/0116486 A1 5/2012 Naga et al.
2012/0123331 A1 5/2012 Satake
2012/0123399 A1 5/2012 Belikov
2012/0143131 A1 6/2012 Tun
2012/0157892 A1 6/2012 Reitmajer et al.
2012/0203255 A1 8/2012 Hawkins et al.
2012/0221013 A1 8/2012 Hawkins et al.
2012/0232409 A1* 9/2012 Stahmann .............. A61B 5/201 600/483
2012/0296367 A1 11/2012 Grovender et al.
2012/0323211 A1 12/2012 Ogle
2012/0330293 A1 12/2012 Arai
2013/0030431 A1 1/2013 Adams
2013/0030447 A1 1/2013 Adams
2013/0041355 A1 2/2013 Heeren et al.
2013/0046207 A1 2/2013 Capelli
2013/0046293 A1 2/2013 Arai et al.
2013/0053762 A1 2/2013 Rontal et al.
2013/0060234 A1 3/2013 Besser
2013/0110003 A1 5/2013 Surti
2013/0116714 A1 5/2013 Adams et al.
2013/0165764 A1 6/2013 Scheuermann
2013/0190803 A1 7/2013 Angel et al.
2013/0197614 A1 8/2013 Gustus
2013/0218054 A1 8/2013 Sverdlik et al.
2013/0226131 A1 8/2013 Bacino et al.
2013/0253466 A1 9/2013 Campbell
2013/0274726 A1 10/2013 Takayama
2013/0345617 A1 12/2013 Wallace
2014/0005576 A1 1/2014 Adams
2014/0005706 A1 1/2014 Gelfand et al.
2014/0012186 A1 1/2014 Thyzel
2014/0039002 A1 2/2014 Diodone et al.
2014/0039358 A1 2/2014 Zhou et al.
2014/0039513 A1 2/2014 Hakala
2014/0046229 A1 2/2014 Hawkins et al.
2014/0046353 A1 2/2014 Adams
2014/0052146 A1 2/2014 Curtis et al.
2014/0052147 A1 2/2014 Hakala et al.
2014/0058294 A1 2/2014 Gross et al.
2014/0074111 A1 3/2014 Hakala
2014/0128848 A1 5/2014 Appling et al.
2014/0153087 A1 6/2014 Hutchings et al.
2014/0155990 A1 6/2014 Nyuli
2014/0180069 A1 6/2014 Millett
2014/0180126 A1 6/2014 Millett
2014/0180134 A1 6/2014 Hoseit
2014/0188094 A1 7/2014 Islam
2014/0228829 A1 8/2014 Schmitt
2014/0257144 A1 9/2014 Capelli et al.
2014/0257148 A1 9/2014 Jie
2014/0276573 A1 9/2014 Miesel
2014/0288570 A1 9/2014 Adams
2014/0309536 A1 10/2014 Douk et al.
2014/0336626 A1 11/2014 Jiang
2014/0336637 A1 11/2014 Agrawal
2014/0357997 A1 12/2014 Hartmann
2015/0003900 A1 1/2015 Ullrich et al.
2015/0005576 A1 1/2015 Diodone et al.
2015/0039002 A1 2/2015 Hawkins
2015/0057648 A1 2/2015 Swift et al.
2015/0071591 A1 3/2015 Chen
2015/0073430 A1 3/2015 Hakala et al.
2015/0080875 A1 3/2015 Kasprzyk et al.
2015/0100048 A1 4/2015 Hiereth et al.
2015/0105715 A1 4/2015 Pikus et al.
2015/0119870 A1 4/2015 Rudie
2015/0126990 A1 5/2015 Sharma
2015/0141764 A1 5/2015 Harks et al.
2015/0250542 A1 9/2015 Islam
2015/0276689 A1 10/2015 Watanabe et al.
2015/0313732 A1 11/2015 Fulton, III
2015/0320432 A1 11/2015 Adams
2015/0342678 A1 12/2015 Deladurantaye et al.
2015/0342681 A1 12/2015 Lee
2015/0359432 A1 12/2015 Ehrenreich
2015/0359557 A1 12/2015 Shimokawa
2016/0008016 A1 1/2016 Cioanta et al.
2016/0016016 A1 1/2016 Taylor et al.
2016/0018602 A1 1/2016 Govari et al.
2016/0022294 A1 1/2016 Cioanta et al.
2016/0038087 A1 2/2016 Hunter
2016/0095610 A1 4/2016 Lipowski et al.
2016/0135828 A1 5/2016 Hawkins et al.
2016/0135891 A1 5/2016 Feldman
2016/0143522 A1 5/2016 Ransbury
2016/0151639 A1 6/2016 Scharf et al.
2016/0183819 A1 6/2016 Burnett
2016/0183957 A1 6/2016 Hakala et al.
2016/0184020 A1 6/2016 Kowalewski et al.
2016/0184022 A1 6/2016 Grace et al.
2016/0184023 A1 6/2016 Grace et al.
2016/0184526 A1 6/2016 Beyar
2016/0184570 A1 6/2016 Grace et al.
2016/0228187 A1 8/2016 Gross
2016/0234534 A1 8/2016 Kitahara et al.
2016/0262784 A1 9/2016 Grace et al.
2016/0270806 A1 9/2016 Wallace
2016/0302762 A1 10/2016 Stigall et al.
2016/0324564 A1 11/2016 Gerlach et al.
2016/0331389 A1 11/2016 Hakala et al.
2016/0339204 A1 11/2016 Williams
2016/0367274 A1 12/2016 Wallace
2016/0367275 A1 12/2016 Wallace
2017/0049463 A1 2/2017 Popovic et al.
2017/0056035 A1 3/2017 Adams
2017/0086867 A1 3/2017 Adams
2017/0119469 A1 5/2017 Shimizu et al.
2017/0119470 A1 5/2017 Diamant et al.
2017/0135709 A1 5/2017 Nguyen et al.
2017/0151421 A1 6/2017 Asher
2017/0192242 A1 7/2017 Laycock
2017/0209050 A1 7/2017 Fengler et al.
2017/0265942 A1 9/2017 Grace et al.
2017/0303946 A1 10/2017 Ku et al.
2017/0311965 A1 11/2017 Adams
2018/0008348 A1 1/2018 Grace et al.
2018/0042661 A1 2/2018 Long
2018/0042677 A1 2/2018 Yu et al.
2018/0045897 A1 2/2018 Chia
2018/0049877 A1 2/2018 Venkatasubramanian
2018/0085174 A1 3/2018 Radtke et al.
2018/0092763 A1 4/2018 Dagan et al.
2018/0095287 A1 4/2018 Jeng et al.
2018/0098779 A1 4/2018 Betelia et al.
2018/0152568 A1 5/2018 Thumpudi et al.
2018/0169392 A1 6/2018 Franklin
2018/0214677 A1 8/2018 Tarunaga
2018/0238675 A1 8/2018 Wan
2018/0256250 A1 9/2018 Adams et al.
2018/0280005 A1 10/2018 Parmentier
2018/0303501 A1 10/2018 Hawkins
2018/0303503 A1 10/2018 Eggert et al.
2018/0303504 A1 10/2018 Eggert et al.
2018/0304053 A1 10/2018 Eggert et al.
2018/0323571 A1 11/2018 Brown et al.
2018/0333043 A1 11/2018 Teriluc
2018/0360482 A1 12/2018 Nguyen
2019/0029702 A1 1/2019 De Cicco
2019/0029703 A1 1/2019 Wasdyke et al.
2019/0069916 A1 3/2019 Hawkins et al.
2019/0072378 A1 3/2019 Hane et al.
2019/0097380 A1 3/2019 Luft et al.
2019/0099588 A1 4/2019 Ramanath et al.
2019/0104933 A1 4/2019 Stern
2019/0117242 A1 4/2019 Lawinger
2019/0150960 A1 5/2019 Nguyen et al.
2019/0150961 A1 5/2019 Tozzi
2019/0159792 A1 5/2019 Panian
2019/0167349 A1 6/2019 Shamay
2019/0175111 A1 6/2019 Genereux et al.
2019/0175300 A1 6/2019 Horn et al.
2019/0175372 A1 6/2019 Boyden et al.
2019/0175407 A1 6/2019 Bacher

(56) References Cited

U.S. PATENT DOCUMENTS

2019/0209368 A1 7/2019 Park et al.
2019/0232066 A1 8/2019 Lim et al.
2019/0247680 A1 8/2019 Mayer
2019/0262594 A1 8/2019 Ogata et al.
2019/0265419 A1 8/2019 Tayebati
2019/0282249 A1 9/2019 Tran et al.
2019/0282250 A1 9/2019 Tran et al.
2019/0285803 A1 9/2019 Van Zuylen
2019/0321100 A1 10/2019 Masotti et al.
2019/0321101 A1 10/2019 Massoti et al.
2019/0328259 A1 10/2019 Deno et al.
2019/0365400 A1 12/2019 Adams et al.
2019/0380589 A1 12/2019 Lloret
2019/0388002 A1 12/2019 Bozsak et al.
2019/0388110 A1 12/2019 Nguyen et al.
2019/0388133 A1 12/2019 Sharma
2019/0388151 A1 12/2019 Bhawalkar
2019/0388654 A1 12/2019 Chou
2020/0000484 A1 1/2020 Hawkins
2020/0008856 A1 1/2020 Harmouche
2020/0022754 A1* 1/2020 Cottone ............ A61B 17/0218
2020/0038087 A1 2/2020 Harmouche
2020/0046429 A1 2/2020 Tschida et al.
2020/0046949 A1 2/2020 Chisena et al.
2020/0054352 A1 2/2020 Brouillette et al.
2020/0060814 A1 2/2020 Murphy
2020/0061931 A1 2/2020 Brown et al.
2020/0069371 A1 3/2020 Brown et al.
2020/0085458 A1 3/2020 Nguyen et al.
2020/0085459 A1 3/2020 Adams
2020/0101269 A1 4/2020 Hayes
2020/0107960 A1 4/2020 Bacher
2020/0108236 A1 4/2020 Salazar et al.
2020/0129195 A1 4/2020 McGowan et al.
2020/0129741 A1 4/2020 Kawwas
2020/0155812 A1 5/2020 Zhang et al.
2020/0197019 A1 6/2020 Harper
2020/0205890 A1 7/2020 Harlev
2020/0246032 A1 8/2020 Betelia et al.
2020/0289202 A1 9/2020 Miyagawa et al.
2020/0297366 A1 9/2020 Nguyen et al.
2020/0337717 A1 10/2020 Walzman
2020/0345380 A1 11/2020 Boyle et al.
2020/0383724 A1 12/2020 Adams et al.
2020/0397230 A1 12/2020 Massimini et al.
2020/0397453 A1 12/2020 McGowan et al.
2020/0398033 A1 12/2020 McGowan et al.
2020/0405333 A1 12/2020 Massimini et al.
2020/0405391 A1 12/2020 Massimini et al.
2020/0406009 A1 12/2020 Massimini et al.
2020/0406010 A1 12/2020 Massimini et al.
2021/0038237 A1 2/2021 Adams
2021/0085347 A1 3/2021 Phan et al.
2021/0085348 A1 3/2021 Nguyen
2021/0085383 A1 3/2021 Vo et al.
2021/0116302 A1 4/2021 Jean-Ruel
2021/0128241 A1 5/2021 Schultheis
2021/0137598 A1 5/2021 Cook
2021/0153939 A1 5/2021 Cook
2021/0177442 A1 6/2021 Girdhar et al.
2021/0177445 A1 6/2021 Nguyen
2021/0186613 A1 6/2021 Cook
2021/0212765 A1 7/2021 Verhagen
2021/0220052 A1 7/2021 Cook
2021/0220053 A1 7/2021 Cook
2021/0244473 A1 8/2021 Cook et al.
2021/0267685 A1 9/2021 Schultheis
2021/0275247 A1 9/2021 Schultheis
2021/0275249 A1 9/2021 Massimini et al.
2021/0282792 A1 9/2021 Adams et al.
2021/0290259 A1 9/2021 Hakala et al.
2021/0290286 A1 9/2021 Cook
2021/0290305 A1 9/2021 Cook
2021/0298603 A1 9/2021 Feldman
2021/0338258 A1 11/2021 Hawkins et al.
2021/0353359 A1 11/2021 Cook
2021/0369348 A1 12/2021 Cook
2021/0378743 A1 12/2021 Massimini et al.
2021/0378744 A1 12/2021 Fanier et al.
2021/0386479 A1 12/2021 Massimini et al.
2022/0000505 A1 1/2022 Hauser
2022/0000506 A1 1/2022 Hauser
2022/0000507 A1 1/2022 Hauser
2022/0000508 A1 1/2022 Schmitt et al.
2022/0000509 A1 1/2022 Laser et al.
2022/0000551 A1 1/2022 Govari et al.
2022/0001138 A1 1/2022 Howell
2022/0008130 A1 1/2022 Massimini et al.
2022/0008693 A1 1/2022 Humbert et al.
2022/0015785 A1 1/2022 Hakala et al.
2022/0021190 A1 1/2022 Pecquois
2022/0022902 A1 1/2022 Spano
2022/0022912 A1 1/2022 Efremkin
2022/0023528 A1 1/2022 Long et al.
2022/0040454 A1 2/2022 Hamm
2022/0054194 A1 2/2022 Bacher et al.
2022/0071704 A1 3/2022 Le
2022/0168594 A1 6/2022 Mayer
2022/0183738 A1 6/2022 Flores et al.
2022/0218402 A1 7/2022 Schultheis
2022/0249165 A1 8/2022 Cook
2022/0249166 A1 8/2022 Cook et al.
2022/0273324 A1 9/2022 Schultheis
2022/0287732 A1 9/2022 Anderson et al.
2022/0313293 A1 10/2022 Singh
2022/0313359 A1 10/2022 Schultheis et al.
2022/0338890 A1 10/2022 Anderson et al.
2022/0354578 A1 11/2022 Cook
2022/0387106 A1 12/2022 Cook
2023/0013920 A1 1/2023 Massimini
2023/0064371 A1 3/2023 Cook et al.
2023/0137107 A1 5/2023 Cook et al.
2023/0157754 A1 5/2023 Bacher et al.
2023/0200906 A1 6/2023 Cook et al.
2023/0233256 A1 7/2023 Cook et al.
2023/0240748 A1 8/2023 Cook et al.
2023/0248376 A1 8/2023 Anderson et al.
2023/0255635 A1 8/2023 Schultheis et al.
2023/0255688 A1 8/2023 Schultheis et al.
2023/0255689 A1 8/2023 Schultheis et al.
2023/0310054 A1 10/2023 Schultheis
2023/0310067 A1 10/2023 Schultheis et al.
2023/0310073 A1 10/2023 Adams et al.
2023/0320576 A1 10/2023 Feldman
2023/0338088 A1 10/2023 Massimini et al.
2023/0338089 A1 10/2023 Schultheis
2023/0414234 A1 12/2023 Anderson et al.
2024/0001076 A1 1/2024 Gelsinger
2024/0016508 A1 1/2024 Kocur
2024/0016544 A1 1/2024 Schultheis et al.
2024/0016545 A1 1/2024 Schultheis et al.
2024/0023813 A1 1/2024 Milner
2024/0032995 A1 2/2024 Schultheis et al.
2024/0033002 A1 2/2024 Cook
2024/0041520 A1 2/2024 Schultheis et al.
2024/0050170 A1 2/2024 Fournier
2024/0050696 A1 2/2024 Japuntich
2024/0058060 A1 2/2024 Cook et al.
2024/0065711 A1 2/2024 Hendrickson
2024/0065712 A1 2/2024 Schultheis
2024/0099773 A1 3/2024 Schabert
2024/0122648 A1 4/2024 Cook
2024/0165658 A1 5/2024 Fu
2024/0173044 A1 5/2024 Chen et al.
2024/0173526 A1 5/2024 Kofidis
2024/0189543 A1 6/2024 Salinas
2024/0216062 A1 7/2024 Cook
2024/0260981 A1 8/2024 Betelia
2024/0260982 A1 8/2024 Peterson
2024/0277410 A1 8/2024 Cook
2024/0277974 A1 8/2024 Oehler
2024/0277980 A1 8/2024 O'Neill
2024/0285296 A1 8/2024 Vo
2024/0285922 A1 8/2024 Chu

(56) References Cited

U.S. PATENT DOCUMENTS

| | | | |
|---|---|---|---|
| 2024/0299051 | A1 | 9/2024 | Sidhu et al. |
| 2024/0307119 | A1 | 9/2024 | Nguyen |
| 2024/0325045 | A1 | 10/2024 | Otake |
| 2024/0382258 | A1 | 11/2024 | Schultheis |
| 2025/0025237 | A1 | 1/2025 | Cook |
| 2025/0040947 | A1 | 2/2025 | Schultheis |

FOREIGN PATENT DOCUMENTS

| | | | |
|---|---|---|---|
| CA | 2229806 | | 3/1997 |
| CA | 2281519 | | 8/1998 |
| CA | 2983655 | | 10/2016 |
| CA | 3209797 | | 9/2022 |
| CN | 102057422 | | 5/2011 |
| CN | 109223100 | | 1/2019 |
| CN | 110638501 | | 1/2020 |
| CN | 110638501 | A | 1/2020 |
| CN | 106794043 | | 3/2020 |
| CN | 107411805 | | 1/2022 |
| CN | 107899126 | | 1/2022 |
| CN | 109475378 | | 1/2022 |
| CN | 113876388 | | 1/2022 |
| CN | 113877044 | | 1/2022 |
| CN | 113907838 | | 1/2022 |
| CN | 113951972 | A | 1/2022 |
| CN | 113951973 | A | 1/2022 |
| CN | 113974765 | | 1/2022 |
| CN | 113974826 | A | 1/2022 |
| CN | 113993463 | | 1/2022 |
| CN | 215384399 | | 1/2022 |
| CN | 215386905 | | 1/2022 |
| CN | 215458400 | | 1/2022 |
| CN | 215458401 | | 1/2022 |
| CN | 215505065 | | 1/2022 |
| CN | 215534803 | | 1/2022 |
| CN | 215537694 | | 1/2022 |
| CN | 215584286 | | 1/2022 |
| CN | 215606068 | | 1/2022 |
| CN | 215651393 | | 1/2022 |
| CN | 215651394 | | 1/2022 |
| CN | 215651484 | | 1/2022 |
| CN | 215653328 | | 1/2022 |
| CN | 114053552 | | 2/2022 |
| CN | 115175625 | | 10/2022 |
| CN | 117752412 | | 3/2024 |
| CN | 118055734 | | 5/2024 |
| DE | 3038445 | A1 | 5/1982 |
| DE | 3836337 | A1 | 4/1990 |
| DE | 3913027 | A1 | 10/1990 |
| DE | 69431758 | | 1/2003 |
| DE | 10230626 | | 1/2004 |
| DE | 202008016760 | | 3/2009 |
| DE | 102007046902 | | 4/2009 |
| DE | 102008034702 | | 1/2010 |
| DE | 102009007129 | | 8/2010 |
| DE | 202010009899 | | 11/2010 |
| DE | 102013201928 | | 8/2014 |
| DE | 102020117713 | | 1/2022 |
| EP | 0119296 | | 9/1984 |
| EP | 0261831 | B1 | 6/1992 |
| EP | 558297 | A2 | 9/1993 |
| EP | 0571306 | A1 | 11/1993 |
| EP | 0547146 | | 7/1995 |
| EP | 1179993 | A1 | 2/2002 |
| EP | 1946712 | | 7/2008 |
| EP | 1946712 | A1 | 7/2008 |
| EP | 1453566 | | 9/2008 |
| EP | 2157569 | | 2/2010 |
| EP | 2470248 | | 7/2012 |
| EP | 2879595 | | 6/2015 |
| EP | 2879595 | A1 | 6/2015 |
| EP | 2944264 | A1 | 6/2015 |
| EP | 3226795 | A1 | 10/2017 |
| EP | 3266487 | | 1/2018 |
| EP | 3318204 | | 5/2018 |
| EP | 2879607 | | 2/2019 |
| EP | 3461438 | A1 | 4/2019 |
| EP | 3473195 | A1 | 4/2019 |
| EP | 2961463 | | 5/2019 |
| EP | 3240603 | | 5/2019 |
| EP | 3197381 | | 3/2020 |
| EP | 3643260 | A1 | 4/2020 |
| EP | 3240494 | | 3/2021 |
| EP | 3522812 | | 12/2021 |
| EP | 3076881 | B1 | 1/2022 |
| EP | 3932342 | | 1/2022 |
| EP | 3936140 | | 1/2022 |
| EP | 3960099 | | 3/2022 |
| EP | 4051154 | | 9/2022 |
| EP | 4129213 | | 2/2023 |
| EP | 4277537 | | 11/2023 |
| EP | 4297669 | | 1/2024 |
| EP | 4146322 | | 4/2024 |
| EP | 3182931 | | 6/2024 |
| EP | 3950036 | | 8/2024 |
| EP | 4034005 | | 12/2024 |
| GB | 1082397 | | 9/1967 |
| JP | S62275446 | A | 11/1987 |
| JP | H05264763 | | 10/1993 |
| JP | 1996089511 | | 4/1996 |
| JP | H09117407 | | 5/1997 |
| JP | 2001520070 | | 10/2001 |
| JP | 2004519296 | | 7/2004 |
| JP | 2008506447 | | 3/2008 |
| JP | 2008083273 | | 4/2008 |
| JP | 2009519777 | | 5/2009 |
| JP | 2009213589 | | 9/2009 |
| JP | 2011524203 | | 9/2011 |
| JP | 4805208 | | 11/2011 |
| JP | 4808620 | | 11/2011 |
| JP | 2012505050 | | 3/2012 |
| JP | 2014123147 | | 7/2014 |
| JP | A2014516614 | | 7/2014 |
| JP | A2015522344 | | 8/2015 |
| JP | 2015217215 | | 12/2015 |
| JP | 2018538077 | | 12/2018 |
| JP | 2024511710 | | 3/2024 |
| KR | 20050098932 | | 10/2005 |
| KR | 20080040111 | | 5/2008 |
| KR | 20160090877 | A | 8/2016 |
| KR | 20180054041 | | 5/2018 |
| WO | WO9007904 | A1 | 7/1990 |
| WO | WO9105332 | A1 | 4/1991 |
| WO | 9203095 | A1 | 3/1992 |
| WO | WO9208515 | | 5/1992 |
| WO | WO9524867 | | 9/1995 |
| WO | 1999002095 | A1 | 1/1999 |
| WO | 1999020189 | A1 | 4/1999 |
| WO | WO200067648 | | 11/2000 |
| WO | WO2000067648 | A1 | 11/2000 |
| WO | WO0103599 | | 1/2001 |
| WO | WO0103599 | A2 | 1/2001 |
| WO | 20060006169 | A2 | 1/2006 |
| WO | WO2006006169 | | 1/2006 |
| WO | WO2009121017 | | 10/2009 |
| WO | WO2009149321 | A1 | 12/2009 |
| WO | WO2009152352 | | 12/2009 |
| WO | 2010042653 | A1 | 4/2010 |
| WO | WO2011094379 | | 8/2011 |
| WO | 20110126580 | A2 | 10/2011 |
| WO | WO2011126580 | A3 | 10/2011 |
| WO | WO2012025833 | | 3/2012 |
| WO | WO2012042619 | | 4/2012 |
| WO | WO20120052924 | A1 | 4/2012 |
| WO | WO2012058156 | | 5/2012 |
| WO | WO20120120495 | A2 | 9/2012 |
| WO | WO2013119662 | | 8/2013 |
| WO | 20130169807 | A1 | 11/2013 |
| WO | WO2013169807 | | 11/2013 |
| WO | WO2014025397 | A1 | 2/2014 |
| WO | WO20140022867 | A1 | 2/2014 |
| WO | WO2014138582 | | 9/2014 |
| WO | WO2015056662 | | 4/2015 |
| WO | WO2015097251 | A2 | 7/2015 |

(56) References Cited

FOREIGN PATENT DOCUMENTS

| | | |
|---|---|---|
| WO | 20150177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256693 | 12/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | WO2021086571 A1 | 5/2021 |
| WO | WO2021096922 A1 | 5/2021 |
| WO | WO2021101766 | 5/2021 |
| WO | WO2021101766 A1 | 5/2021 |
| WO | WO2021126762 A1 | 6/2021 |
| WO | WO2021150502 A1 | 7/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |
| WO | WO2024079108 | 4/2024 |
| WO | WO2024107418 | 5/2024 |

OTHER PUBLICATIONS

Daemen, J., Tovar Forero, M.N, “The Coronary Intravascular Lithotripsy System”, ICR Journal, 2019; 14(3); 174-181.

Butt, N., Khalid, N., Shlofmitz, E., “Intravascular Lithotripsy”; NCBI Bookshelf. A service of the National Library of Medicine, National Institutes of Health; StatPearls Publishing, 2023.

PathFinder Digital, “Free Space Optics vs. Fiber Optics”, 2023.

International Search Report and Written Opinion, issued in Application Serial No. PCT/US2023/016152, dated Jul. 12, 2023.

Vogel, A., et al. “Intraocular Photodisruption With Picosecond and Nanosecond Laser Pulses: Tissue Effects in Cornea, Lens, and Retina”, Investigative Ophthalmology & Visual Science, Jun. 1994, pp. 3032-3044, vol. 35, No. 7, Association for Research in Vision and Ophthalmology.

Jones, H. M., et al. “Pulsed dielectric breakdown of pressurized water and salt solutions”, Journal of Applied Physics, Jun. 1998, pp. 795-805, vol. 77, No. 2, American Institute of Physics.

Kozulin, I., et al. “The dynamic of the water explosive vaporization on the flat microheater”, Journal of Physics: Conference Series, 2018, pp. 1-4, IOP Publishing, Russia.

Cross, F., “Laser Angioplasty”, Vascular Medicine Review, 1992, pp. 21-30, Edward Arnold.

Doukas, A. G., et al. “Laser-generated stress waves and their effects on the cell membrane”, IEEE Journal of Selected Topics in Quantum Electronics, 1999, pp. 997-1003, vol. 5, Issue 4, IEEE.

Noack, J., et al. “Laser-Induced Plasma Formation in Water at Nanosecond to Femtosecond Time Scales: Calculation of Thresholds, Absorption Coefficients, and Energy Density”, IEEE Journal of Quantum Electronics, 1999, pp. 1156-1167, vol. 35, No. 8, IEEE.

Pratsos, A., “The use of Laser for the treatment of coronary artery disease”, Bryn Mawr Hospital, 2010.

Li, Xian-Dong, et al. “Influence of deposited energy on shock wave induced by underwater pulsed current discharge”, Physics of Plasmas, 2016, vol. 23, American Institute of Physics.

Logunov, S., et al. “Light diffusing optical fiber illumination”, Renewable Energy and the Environment Congress, 2013, Corning, NY, USA.

Maxwell, A. D., et al. “Cavitation clouds created by shock scattering from bubbles during histotripsy”, Acoustical Society of America, 2011, pp. 1888-1898, vol. 130, No. 4, Acoustical Society of America.

Mcateer, James A., et al. “Ultracal-30 Gypsum Artificial Stones For Research On The Mechinisms Of Stone Breakage In Shock Wave Lithotripsy”, 2005, pp. 429-434, Springer-Verlag.

Vogel, A., et al. “Mechanisms of Intraocular Photodisruption With Picosecond and Nanosecond Laser Pulses”, Lasers in Surgery and Medicine, 1994, pp. 32-43, vol. 15, Wiley-Liss Inc., Lubeck, Germany.

Vogel, A., et al. “Mechanisms of Pulsed Laser Ablation of Biological Tissues”, Chemical Reviews, 2003, pp. 577-644, vol. 103, No. 2, American Chemical Society.

Medlight, “Cylindrical light diffuser Model RD-ML”, Medlight S.A., Switzerland. 2015.

Medlight, “Cylindircal light diffuser Model RD”, Medlight S.A., Switzerland. 2015.

Mayo, Michael E., “Interaction of Laser Radiation with Urinary Calculi”, Cranfield University Defense and Security, PhD Thesis, 2009, Cranfield University.

Vogel, A., et al. “Minimization of Cavitation Effects in Pulsed Laser Ablation Illustrated on Laser Angioplasty”, Applied Physics, 1996, pp. 173-182, vol. 62, Springer-Verlag.

Mirshekari, G., et al. “Microscale Shock Tube”, Journal of Microelectromechanical Systems, 2012, pp. 739-747, vol. 21, No. 3, IEEE.

“Polymicro Sculpted Silica Fiber Tips”, Molex, 2013, Molex.

Zhou, J., et al. “Optical Fiber Tips and Their Applications”, Polymicro Technologies A Subsidiary of Molex, Nov. 2007.

Liang, Xiao-Xuan, et al. “Multi-Rate-Equation modeling of the energy spectrum of laser-induced conduction band electrons in water”, Optics Express, 2019, vol. 27, No. 4, Optical Society of America.

Nachabe, R., et al. “Diagnosis of breast cancer using diffuse optical spectroscopy from 500 to 1600 nm: comparison of classification methods”, Journal of Biomedical Optics, 2011, vol. 16(8), SPIE.

Naugol’nykh, K. A., et al. “Spark Discharges in Water”, Academy of Sciences USSR Institute of Acoustics, 1971, Nauka Publishing Co., Moscow, USSR.

Van Leeuwen, Ton G., et al. “Noncontact Tissue Ablation by Holmium: YSGG Laser Pulses in Blood”, Lasers in Surgery and Medicine, 1991, vol. 11, pp. 26-34, Wiley-Liss Inc.

(56) References Cited

OTHER PUBLICATIONS

Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing. Oct. 2015.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion, issued by the EP/ISA, in PCT/US2021/048819, dated Jan. 14, 2022.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.

(56) References Cited

OTHER PUBLICATIONS

Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and On Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method For Fabricating Artificial Kidney Stones Of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.

(56) References Cited

OTHER PUBLICATIONS

Smith, A., et al. "Deterministic Nanosecond Laser-Induced Break-down Thresholds In Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", Spie Bios, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany. Dec. 2, 2021.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery Of Atrial Endocardial Potential Maps From Non-contact Electrode Data." Auckland Bioengineering Institute. (ID 1421). May 2019.
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019.
Sacher et al., "Comparison Of Manual Vs Automatic Annotation To Identify Abnormal Substrate For Scar Related VT Ablation." LIRYC Institute, Bordeaux University Hospital, France (ID 1336). Poster for conference in San Francisco, May 8-11, 2019.

(56) References Cited

OTHER PUBLICATIONS

Oriel Instruments, "Introduction to Beam Splitters for Optical Research Applications", Apr. 2014, pp. 1-9, https://www.azoptics.com/Article.aspx?ArticalD=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Aug. 20, 2021 in PCT Application Serial No. PCT/US2021/031130.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
International Search Report and Written Opinion dated Aug. 25, 2022 in PCT Application Serial No. PCTUS/2022/028035.
International Search Report and Written Opinion dated Sep. 15, 2022 in PCT Application Serial No. PCTUS/2022/032045.
International Search Report and Written Opinion dated Nov. 8, 2022 in PCT Application Serial No. PCTUS/2022/039678.
International Search Report and Written Opinion, PCT Application Serial No. PCT/US2022/047751 issued Feb. 10, 2023, by the European Patent Office.
International Search Report and Written Opinion, PCT Application Serial No. PCT/US2022/047691 issued Feb. 13, 2023, by the European Patent Office.
Accucoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023.
International Search Report and Written Opinion issued by the European Patent Office, for Serial No. PCT/US2023/011497, dated Apr. 28, 2023.
International Search Report and Written Opinion issued by the European Patent Office, for Serial No. PCT/US2023/012599, dated May 19, 2023.
All Foreign References and Non-Patent Literature are Available in the Parent Application, U.S. Appl. No. 17/211,150. The Examiner Has Access to These Materials Through the PTO Computer Systems. If Additional Copies Are Desired, Please Notify Applicants Through Their Attorneys.
"Custom Medical Skived Tubing", Duke Extrusion, 2025. https://www.dukeextrusion.com/tubing-options/skived-tubing.
Shen, Yajie et al. "High-peak-power and narrow-linewidth Q-switched Ho: YAG laser in-band pumped at 1931 nm." Applied Physics Express 13.5 (2020): 052006. (Year 2020).

* cited by examiner 109
412
418
107
404D
432
430
422A
404
106
105
404P
446
460

438
402
422A
428
456
410
458
440
422
436
412
462
427
425
422A
442
426
423
424
400

ELECTRICAL ANALYZER ASSEMBLY FOR INTRAVASCULAR LITHOTRIPSY DEVICE

RELATED APPLICATIONS

This application is a continuation application of and claims priority on U.S. patent application Ser. No. 17/211,150, filed on Mar. 24, 2021, now U.S. Pat. No. 11,707,323 and entitled "ELECTRICAL ANALYZER ASSEMBLY FOR INTRAVASCULAR LITHOTRIPSY DEVICE". Additionally, U.S. patent application Ser. No. 17/211,150, now U.S. Pat. No. 11,707,323, claims priority on U.S. Provisional Application Ser. No. 63/004,977, filed on Apr. 3, 2020. As far as permitted, the contents of U.S. patent application Ser. No. 17/211,150, now U.S. Pat. No. 11,707,323, and U.S. Provisional Application Ser. No. 63/004,977 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a method for treating a treatment site within or adjacent to a vessel wall or heart valve within a body of a patient. In various embodiments, the method includes the steps of generating energy with an energy source; positioning a balloon substantially adjacent to the treatment site, the balloon having a balloon wall that defines a balloon interior that receives a balloon fluid; receiving energy from the energy source with an energy guide; guiding the energy with the energy guide into the balloon interior; monitoring a condition of the balloon with an electrical analyzer assembly while energy is being guided into the balloon interior, the electrical analyzer assembly including (i) a first electrode, (ii) a second electrode that is in fluid communication with blood of the patient, and (iii) an impedance detector that is electrically coupled to the first electrode and the second electrode; and detecting an impedance between the first electrode and the second electrode with the impedance detector.

In some embodiments, the step of monitoring includes analyzing an electrical signal with the electrical analyzer assembly, and determining the condition of the balloon with the electrical analyzer assembly based at least in part on the electrical signal.

In certain embodiments, the step of monitoring includes analyzing an electrical signal with the electrical analyzer assembly, and determining with the electrical analyzer assembly whether a rupture of the balloon has occurred based at least in part on the electrical signal.

In some embodiments, wherein when a rupture in the balloon has not occurred, the step of monitoring includes the steps of positioning the first electrode to be in fluid communication with the balloon fluid in the balloon interior, and positioning the second electrode to be not in fluid communication with the balloon fluid in the balloon interior.

In certain embodiments, the method further includes the step of generating a detector signal with the impedance detector based at least in part on the detected impedance between the first electrode and the second electrode.

In some embodiments, the method further includes the steps of electrically coupling a system controller to the impedance detector; receiving the detector signal from the impedance detector with the system controller; and determining the condition of the balloon with the system controller based at least in part on the detector signal. In alternative embodiments, the step of electrically coupling includes electrically coupling the system controller to the impedance detector via a wired connection, or the step of electrically coupling includes electrically coupling the system controller to the impedance detector via a wireless connection.

In certain embodiments, the method further includes the step of recognizing a normal condition of the balloon with the system controller based at least in part on the detector signal.

In some embodiments, the method further includes the step of recognizing a potential rupture of the balloon with the system controller based at least in part on the detector signal.

In certain embodiments, the method further includes the step of automatically shutting down operation of the catheter system with the system controller upon recognition of the potential rupture of the balloon.

In some embodiments, the step of monitoring includes positioning the first electrode within the balloon interior.

In certain embodiments, the method further includes the step of directing the balloon fluid into the balloon interior via an inflation conduit; and wherein the step of monitoring includes positioning the first electrode within the inflation conduit.

In some embodiments, the method further includes the step of guiding positioning of the balloon substantially adjacent to the treatment site with a guidewire; and wherein the step of monitoring includes positioning the second electrode substantially adjacent to the guidewire.

In certain embodiments, the method further includes the steps of guiding positioning of the balloon substantially adjacent to the treatment site with a guidewire, and moving a guidewire lumen over the guidewire; and wherein the step of monitoring includes positioning the second electrode within the guidewire lumen.

In various embodiments, the step of generating includes the energy source being a laser source that provides pulses of laser energy; and the step of receiving includes the energy guide including an optical fiber.

The present invention is also directed toward a method for treating a treatment site within or adjacent to a vessel wall or heart valve within a body of a patient, the method including the steps of generating energy with an energy source; positioning a balloon substantially adjacent to the treatment site, the balloon having a balloon wall that defines a balloon interior that receives a balloon fluid; directing the balloon fluid into the balloon interior through an inflation conduit; receiving energy from the energy source with an energy guide; guiding the energy with the energy guide into the balloon interior; monitoring a condition of the balloon with an electrical analyzer assembly while energy is being guided into the balloon interior, the electrical analyzer assembly including (i) a first electrode that is positioned within the inflation conduit, (ii) a second electrode, and (iii)

an impedance detector that is electrically coupled to the first electrode and the second electrode; and detecting an impedance between the first electrode and the second electrode with the impedance detector.

The present invention is further directed toward a method for treating a treatment site within or adjacent to a vessel wall or heart valve within a body of a patient, the method including the steps of generating energy with an energy source; positioning a balloon substantially adjacent to the treatment site, the balloon having a balloon wall that defines a balloon interior that receives a balloon fluid; guiding positioning of the balloon substantially adjacent to the treatment site with a guidewire; receiving energy from the energy source with an energy guide; guiding the energy with the energy guide into the balloon interior; monitoring a condition of the balloon with an electrical analyzer assembly while energy is being guided into the balloon interior, the electrical analyzer assembly including (i) a first electrode, (ii) a second electrode that is positioned substantially adjacent to the guidewire, and (iii) an impedance detector that is electrically coupled to the first electrode and the second electrode; and detecting an impedance between the first electrode and the second electrode with the impedance detector.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
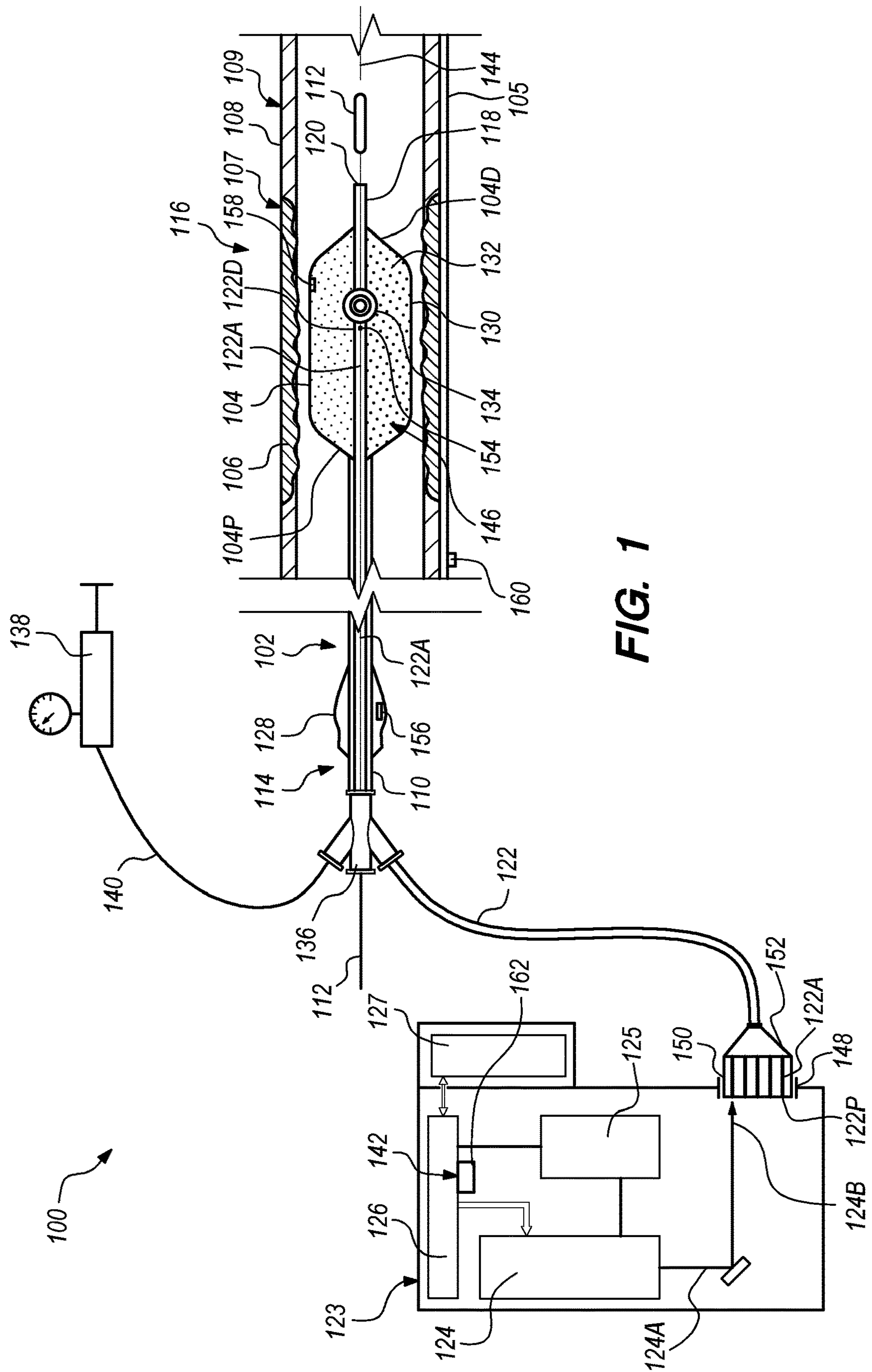
FIG. 1 is a schematic cross-sectional view of an embodiment of a catheter system in accordance with various embodiments herein, the catheter system including an electrical analyzer assembly having features of the present invention.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as “treatment sites”) can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

The catheter systems and related methods disclosed herein are configured to monitor the performance, reliability and safety of an intravascular lithotripsy catheter. In various embodiments, the catheter systems of the present invention utilize an energy source, e.g., a light source such as a laser source or another suitable energy source, which provides energy that is guided by an energy guide, e.g., a light guide, to create a localized plasma in a balloon fluid within a balloon interior of an inflatable balloon of the catheter. As such, the energy guide can sometimes be referred to as, or can be said to incorporate a “plasma generator” at or near a guide distal end of the energy guide that is positioned within the balloon interior. This localized plasma, in turn, induces a high energy bubble inside the balloon interior to create pressure waves to impart pressure onto and induce fractures in a treatment site, such as a calcified vascular lesion or a fibrous vascular lesion, at a treatment site within or adjacent to a blood vessel wall or a heart valve within a body of a patient.

In particular, in various embodiments, the catheter systems can include a catheter configured to advance to the treatment site within or adjacent a blood vessel or heart valve within the body of the patient. The catheter includes a catheter shaft, and a balloon that is coupled and/or secured to the catheter shaft. The inflatable balloons herein can include a balloon wall that defines the balloon interior and can be configured to receive the balloon fluid within the balloon interior to expand from a collapsed configuration suitable for advancing the catheter through a patient’s vasculature, to an expanded configuration suitable for anchoring the catheter in position relative to the treatment site. The catheter systems also include one or more energy guides, e.g., light guides, disposed along the catheter shaft and within the inflatable balloon. Each energy guide can be configured for generating pressure waves within the inflatable balloon for disrupting the treatment sites. The catheter systems utilize energy from an energy source, e.g., light energy from a light source, to generate the plasma, i.e. via the plasma generator, within the balloon fluid at or near a guide distal end of the energy guide disposed in the inflatable balloon located at the treatment site. The plasma formation can initiate a pressure wave and can initiate the rapid formation of one or more bubbles that can rapidly expand to a maximum size and then dissipate through a cavitation event that can launch a pressure wave upon collapse. The rapid expansion of the plasma-induced bubbles can generate one or more pressure waves within the balloon fluid retained within the inflatable balloon and thereby impart pressure waves upon the treatment site. In some embodiments, the energy source can be configured to provide sub-millisecond pulses of energy, e.g., light energy, from the energy source to initiate plasma formation in the balloon fluid within the inflatable balloon to cause rapid bubble formation and to impart pressure waves upon the balloon wall at the treatment site. Thus, the pressure waves can transfer mechanical energy through an incompressible balloon fluid to the treatment site to impart a fracture force on the vascular lesion.

As used herein, the terms "intravascular lesion", "vascular lesion" and "treatment site" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more treatment sites within or adjacent a vessel wall of a blood vessel or a heart valve within a body of a patient. In the embodiment illustrated in FIG. 1, the catheter system 100 can include one or more of a catheter 102, a light guide bundle 122 including one or more light guides 122A, a source manifold 136, a fluid pump 138, a system console 123 including one or more of a light source 124, a power source 125, a system controller 126, and a graphic user interface 127 (a "GUI"), a handle assembly 128, and an electrical analyzer assembly 142.

The catheter 102 is configured to move to a treatment site 106 within or adjacent to a blood vessel 108 within a body 107 of a patient 109. The treatment site 106 can include one or more vascular lesions such as calcified vascular lesions, for example. Additionally, or in the alternative, the treatment site 106 can include vascular lesions such as fibrous vascular lesions.

The catheter 102 can include an inflatable balloon 104 (sometimes referred to herein simply as a "balloon"), a catheter shaft 110 and a guidewire 112. The inflatable balloon 104 can be coupled to the catheter shaft 110. The inflatable balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. The catheter shaft 110 can further include an inflation lumen (not shown). In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the inflatable balloon 104. In some embodiments, each light guide 122A can be an optical fiber and the light source 124 can be a laser. The light source 124 can be in optical communication with the light guides 122A at the proximal portion 114 of the catheter system 100.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, it is further appreciated that the light guides 122A described herein can be disposed uniformly or non-uniformly about the guidewire lumen 118 and/or the catheter shaft 110 to achieve the desired effect in the desired locations.

The inflatable balloon 104 can include a balloon wall 130 that defines a balloon interior 146, and can be inflated with a balloon fluid 132 to expand from a collapsed configuration suitable for advancing the catheter 102 through a patient's vasculature, to an expanded configuration suitable for anchoring the catheter 102 in position relative to the treatment site 106. Stated in another manner, when the inflatable balloon 104 is in the expanded configuration, the balloon wall 130 of the inflatable balloon 104 is configured to be positioned substantially adjacent to the treatment site 106. In some embodiments, the light source 124 of the catheter system 100 can be configured to provide sub-millisecond pulses of light from the light source 124, along the light guides 122A, to a location within the balloon interior 146 of the inflatable balloon 104, thereby inducing plasma formation in the balloon fluid 132 within the balloon interior 146 of the inflatable balloon 104. The plasma formation causes rapid bubble formation, and imparts pressure waves upon the treatment site 106. Exemplary plasma-induced bubbles are shown as bubbles 134 in FIG. 1.

It is appreciated that although the catheter systems 100 illustrated herein are generally described as including a light source 124 and one or more light guides 122A, the catheter system 100 can alternatively include any suitable energy source and energy guides for purposes of generating the desired plasma in the balloon fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, forms the pressure waves within the balloon fluid 132 that are utilized to provide the fracture force onto the treatment site 106. Still alternatively, the energy source 124 and/or the energy guides 122A can have another suitable design and/or configuration.

The balloons 104 suitable for use in the catheter systems 100 described in detail herein include those that can be passed through the vasculature of a patient when in the collapsed configuration. In some embodiments, the balloons 104 herein are made from silicone. In other embodiments, the balloons 104 herein are made from polydimethylsiloxane (PDMS), polyurethane, polymers such as PEBAX™ material available from Arkema, which has a location at King of Prussia, Pennsylvania, USA, nylon, and the like. In some embodiments, the balloons 104 can include those having diameters ranging from one millimeter (mm) to 25 mm in diameter. In some embodiments, the balloons 104 can include those having diameters ranging from at least 1.5 mm to 12 mm in diameter. In some embodiments, the balloons 104 can include those having diameters ranging from at least one mm to five mm in diameter.

Additionally, in some embodiments, the balloons 104 herein can include those having a length ranging from at least five mm to 300 mm. More particularly, in some embodiments, the balloons 104 herein can include those having a length ranging from at least eight mm to 200 mm. It is appreciated that balloons 104 of greater length can be positioned adjacent to larger treatment sites 106, and, thus, may be usable for imparting pressure onto and inducing fractures in larger vascular lesions or multiple vascular lesions at precise locations at the treatment site 106.

Further, the balloons 104 herein can be inflated to inflation pressures of between approximately one atmosphere (atm) and 70 atm. In some embodiments, the balloons 104 herein can be inflated to inflation pressures of from at least 20 atm to 70 atm. In other embodiments, the balloons 104 herein can be inflated to inflation pressures of from at least six atm to 20 atm. In still other embodiments, the balloons 104 herein can be inflated to inflation pressures of from at least three atm to 20 atm. In yet other embodiments, the balloons 104 herein can be inflated to inflation pressures of from at least two atm to ten atm.

Still further, the balloons 104 herein can include those having various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons 104 herein can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Exemplary balloon fluids 132 suitable for use herein can include, but are not limited to one or more of water, saline, contrast medium, fluorocarbons, perfluorocarbons, gases, such as carbon dioxide, and the like. In some embodiments, the balloon fluids 132 described can be used as base inflation fluids. In some embodiments, the balloon fluids 132 include a mixture of saline to contrast medium in a volume ratio of 50:50. In other embodiments, the balloon fluids 132 include a mixture of saline to contrast medium in a volume ratio of 25:75. In still other embodiments, the balloon fluids 132 include a mixture of saline to contrast medium in a volume ratio of 75:25. Additionally, the balloon fluids 132 suitable for use herein can be tailored on the basis of composition, viscosity, and the like in order to manipulate the rate of travel of the pressure waves therein. In certain embodiments, the balloon fluids 132 suitable for use herein are biocompatible. A volume of balloon fluid 132 can be tailored by the chosen light source 124 and the type of balloon fluid 132 used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

Additionally, the balloon fluids 132 herein can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the balloon fluids 132 can include those that include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system. By way of non-limiting examples, various lasers described herein can include neodymium:yttrium-aluminum-garnet (Nd:YAG—emission maximum=1064 nm) lasers, holmium:YAG (Ho:YAG—emission maximum=2.1 μm) lasers, or erbium:YAG (Er:YAG—emission maximum=2.94 μm) lasers. In some embodiments, the absorptive agents used herein can be water soluble. In other embodiments, the absorptive agents used herein are not water soluble. In some embodiments, the absorptive agents used in the balloon fluids 132 herein can be tailored to match the peak emission of the light source 124. Various light sources 124 having emission wavelengths of at least ten nanometers to one millimeter are discussed elsewhere herein.

It is appreciated that the catheter system 100 and/or the light guide bundle 122 disclosed herein can include any number of light guides 122A in optical communication with the light source 124 at the proximal portion 114, and with the balloon fluid 132 within the balloon interior 146 of the inflatable balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A herein can include an optical fiber or flexible light pipe. The light guides 122A herein can be thin and flexible and can allow light signals to be sent with very little loss of strength. The light guides 122A herein can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light along its length from a proximal portion, i.e. a guide proximal end 122P, to a distal portion, i.e. a guide distal end 122D, having at least one optical window (not shown) that is positioned within the balloon interior 146. The light guides 122A can create a light path as a portion of an optical network including the light source 124. The light path within the optical network allows light to travel from one part of the network to another. Both the optical fiber and the flexible light pipe can provide a light path within the optical networks herein.

Further, the light guides 122A herein can assume many configurations about and/or relative to the catheter shaft 110 of the catheters 102 described herein. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A herein can be disposed within one or more light guide lumens within the catheter shaft 110.

Additionally, it is further appreciated that the light guides 122A can be disposed at any suitable positions about the circumference of the guidewire lumen 118 and/or the catheter shaft 110, and the guide distal end 122D of each of the light guides 122A can be disposed at any suitable longitudinal position relative to the length of the inflatable balloon 104 and/or relative to the length of the guidewire lumen 118.

Further, the light guides 122A herein can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. It is appreciated that the direction of the acoustic wave can be tailored by changing an angle of the guide distal end 122D of the light guide 122A.

It is further appreciated that the photoacoustic transducers 154 disposed at the guide distal end 122D of the light guide 122A herein can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. It is also appreciated that the light guide 122A can further include additional photoacoustic transducers 154 disposed along one or more side surfaces of the length of the light guide 122A.

The light guides 122A described herein can further include one or more diverting features or "diverters" (not shown in FIG. 1) within the light guide 122A that are configured to direct light to exit the light guide 122A toward a side surface e.g., at or near the guide distal end 122D of the light guide 122A, and toward the balloon wall 130. A diverting feature can include any feature of the system herein that diverts light from the light guide 122A away from its axial path toward a side surface of the light guide 122A. Additionally, the light guides 122A can each include one or more light windows disposed along the longitudinal or axial surfaces of each light guide 122A and in optical communication with a diverting feature. Stated in another manner, the diverting features herein can be configured to direct light in the light guide 122A toward a side surface, e.g., at or near the guide distal end 122D, where the side surface is in optical communication with a light window. The light windows can include a portion of the light guide 122A that allows light to exit the light guide 122A from within the light guide 122A, such as a portion of the light guide 122A lacking a cladding material on or about the light guide 122A.

Examples of the diverting features suitable for use herein include a reflecting element, a refracting element, and a fiber diffuser. Additionally, the diverting features suitable for focusing light away from the tip of the light guides 122A herein can include, but are not to be limited to, those having a convex surface, a gradient-index (GRIN) lens, and a mirror focus lens. Upon contact with the diverting feature, the light is diverted within the light guide 122A to the photoacoustic transducer 154 that is in optical communication with a side surface of the light guide 122A. As noted, the photoacoustic transducer 154 then converts light energy into an acoustic wave that extends away from the side surface of the light guide 122A.

The source manifold 136 can be positioned at or near the proximal portion 114 of the catheter system 100. The source manifold 136 can include one or more proximal end openings that can receive the plurality of light guides 122A of the light guide bundle 122, the guidewire 112, and/or an inflation conduit 140 that is coupled in fluid communication with the fluid pump 138. The catheter system 100 can also include the fluid pump 138 that is configured to inflate the inflatable balloon 104 with the balloon fluid 132, i.e. via the inflation conduit 140, as needed.

As noted above, in the embodiment illustrated in FIG. 1, the system console 123 includes one or more of the light source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, and the GUI 127 can be provided within the catheter system 100 without the specific need for the system console 123.

Further, as illustrated in FIG. 1, in certain embodiments, at least a portion of the electrical analyzer assembly 142 can also be positioned substantially within the system console 123. Alternatively, components of the electrical analyzer assembly 142 can be positioned in a different manner than what is specifically shown in FIG. 1.

Additionally, as shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the desired mechanical coupling between the light guide bundle 122 and the system console 123.

Further, the light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

As provided herein, the light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, e.g., a pulsed source beam, that can be selectively and/or alternatively directed to and received by each of the light guides 122A in the light guide bundle 122 as an individual guide beam 124B. Alternatively, the catheter system 100 can include more than one light source 124. For example, in one non-exclusive alternative embodiment, the catheter system 100 can include a separate light source 124 for each of the light guides 122A in the light guide bundle 122.

The light source 124 can have any suitable design. In certain embodiments, as noted above, the light source 124 can be configured to provide sub-millisecond pulses of light from the light source 124 that are focused onto a small spot in order to couple it into the guide proximal end 122P of the light guide 122A. Such pulses of light energy are then directed along the light guides 122A to a location within the inflatable balloon 104, thereby inducing plasma formation in the balloon fluid 132 within the balloon interior 146 of the inflatable balloon 104. In particular, the light energy emitted at the guide distal end 122D of the light guide 122A energizes the plasma generator to form the plasma within the balloon fluid 132 within the balloon interior 146. The plasma formation causes rapid bubble formation, and imparts pressure waves upon the treatment site 106. In such embodiments, the sub-millisecond pulses of light from the light source 124 can be delivered to the treatment site 106 at a frequency of between approximately one hertz (Hz) and 5000 Hz. In some embodiments, the sub-millisecond pulses of light from the light source 124 can be delivered to the treatment site 106 at a frequency of between approximately 30 Hz and 1000 Hz. In other embodiments, the sub-millisecond pulses of light from the light source 124 can be delivered to the treatment site 106 at a frequency of between approximately ten Hz and 100 Hz. In yet other embodiments, the sub-millisecond pulses of light from the light source 124 can be delivered to the treatment site 106 at a frequency of between approximately one Hz and 30 Hz. Alternatively, the sub-millisecond pulses of light can be delivered to the treatment site 106 at a frequency that can be greater than 5000 Hz.

It is appreciated that although the light source 124 is typically utilized to provide pulses of light energy, the light source 124 can still be described as providing a single source beam 124A, i.e. a single pulsed source beam.

The light sources 124 suitable for use herein can include various types of light sources including lasers and lamps. Alternatively, as noted above, the light sources 124, as referred to herein, can include any suitable type of energy source.

Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (μs) timescales. It is appreciated that there are many combinations of laser wavelengths, pulse widths and energy levels that can be employed to achieve plasma in the balloon fluid 132 of the catheters 102 described herein. In various embodiments, the pulse widths can include those falling within a range including from at least ten ns to 200 ns. In some embodiments, the pulse widths can include those falling within a range including from at least 20 ns to 100 ns. In other embodiments, the pulse widths can include those falling within a range including from at least one ns to 500 ns.

Additionally, exemplary nanosecond lasers can include those within the UV to IR spectrum, spanning wavelengths of about ten nanometers (nm) to one millimeter (mm). In some embodiments, the light sources 124 suitable for use in the catheter systems 100 herein can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter systems 100 disclosed herein can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In some embodiments, the catheter systems 100 herein can generate pressure waves having maximum pressures in the range of at least two MPa to 50 MPa. In other embodiments, the catheter systems 100 herein can generate pressure waves having maximum pressures in the range of at least two MPa to 30 MPa. In yet other embodiments, the catheter systems 100 herein can generate pressure waves having maximum pressures in the range of at least 15 MPa to 25 MPa.

The pressure waves described herein can be imparted upon the treatment site 106 from a distance within a range from at least 0.1 millimeters (mm) to 25 mm extending radially from the light guides 122A when the catheter 102 is placed at the treatment site 106. In some embodiments, the pressure waves can be imparted upon the treatment site 106 from a distance within a range from at least ten mm to 20 mm extending radially from the light guides 122A when the catheter 102 is placed at the treatment site 106. In other embodiments, the pressure waves can be imparted upon the treatment site 106 from a distance within a range from at least one mm to ten mm extending radially from the light guides 122A when the catheter 102 is placed at the treatment site 106. In yet other embodiments, the pressure waves can be imparted upon the treatment site 106 from a distance within a range from at least 1.5 mm to four mm extending radially from the light guides 122A when the catheter 102 is placed at the treatment site 106. In some embodiments, the pressure waves can be imparted upon the treatment site 106 from a range of at least two MPa to 30 MPa at a distance from 0.1 mm to ten mm. In some embodiments, the pressure waves can be imparted upon the treatment site 106 from a range of at least two MPa to 25 MPa at a distance from 0.1 mm to ten mm.

The power source 125 is electrically coupled to and is configured to provide necessary power to each of the light source 124, the system controller 126, the GUI 127, the handle assembly 128, and the electrical analyzer assembly 142. The power source 125 can have any suitable design for such purposes.

As noted, the system controller 126 is electrically coupled to and receives power from the power source 125. Additionally, the system controller 126 is coupled to and is configured to control operation of each of the light source 124, the GUI 127 and the electrical analyzer assembly 142. The system controller 126 can include one or more processors or circuits for purposes of controlling the operation of at least the light source 124, the GUI 127 and the electrical analyzer assembly 142. For example, the system controller 126 can control the light source 124 for generating pulses of light energy as desired, e.g., at any desired firing rate. Additionally, the system controller 126 can control and/or operate in conjunction with the electrical analyzer assembly 142 to effectively provide real-time continuous monitoring of the performance, reliability and safety of the catheter system 100.

Additionally, the system controller 126 can further be configured to control operation of other components of the catheter system 100, e.g., the positioning of the catheter 102 adjacent to the treatment site 106, the inflation of the inflatable balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is employed as desired to impart pressure onto and induce fractures into the vascular lesions at the treatment site 106. Additionally, the GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time, e.g., during use of the catheter system 100. Further, in various embodiments, the GUI 127 can include one or more colors, different sizes, varying brightness, etc., that may act as alerts to the user or operator. Additionally, or in the alternative, the GUI 127 can provide audio data or information to the user or operator. It is appreciated that the specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. Additionally, in this embodiment, the handle assembly 128 is coupled to the inflatable balloon 104 and is positioned spaced apart from the inflatable balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the light source 124, the fluid pump 138, the GUI 127 and the electrical analyzer assembly 142. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. Additionally, in some embodiments, the circuitry 156 can receive electrical signals or data from the electrical analyzer assembly 142. Further, or in the alternative, the circuitry 156 can transmit such electrical signals or otherwise provide data to the system controller 126.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

As an overview, and as provided in greater detail herein, the electrical analyzer assembly 142 is configured to effectively monitor the performance, reliability and safety of the catheter system 100, in particular one that utilizes an energy source 124 to create a localized plasma which in turn induces a high energy bubble in the balloon fluid 132 within the balloon interior 146 of the inflatable balloon 104. More particularly, as described in detail herein, the electrical analyzer assembly 142 is specifically configured to effectively detect damage to, and/or rupturing or bursting of the inflatable balloon 104 during use of the catheter system 100.

During use of the catheter system 100, the generation of the localized plasma and the subsequent inducement of high energy bubbles in the balloon fluid 132 within the balloon interior 146 can cause the balloon fluid to heat up substantially, which, in addition to the pressure waves that are generated within the balloon interior 146, can put substantial stresses onto the balloon wall 130 of the inflatable balloon 104. Thus, the present invention is utilized to detect and/or identify when such stresses ultimately cause damage to the inflatable balloon 104, especially in the form of the potential rupturing or bursting of the inflatable balloon 104. As provided herein, if the electrical analyzer assembly 142 provides an indication, e.g., to the system controller 126, that the inflatable balloon 104 has ruptured, it is important and necessary that the procedure be stopped immediately, as such a failure presents a substantial risk to the patient 109, including potential harms such as tissue burns. Thus, with the invention described herein, the rupture of the inflatable balloon 104 can be quickly and successfully detected, and an indicator or signal can be provided that is used to lock out the energy source 124. This provides a necessary safety interlock for a potentially hazardous condition in which the balloon fluid 132 is able to leak out.

The design of the electrical analyzer assembly 142 can be varied to suit the specific requirements of the catheter system 100. In various embodiments, as described herein, the electrical analyzer assembly 142 can include one or more of a first electrode 158, a second electrode 160, and an impedance detector 162. Alternatively, the electrical analyzer assembly 142 can include more components or fewer components than what is specifically illustrated and described herein.

The first electrode 158 can be positioned at any suitable location within the catheter system 100 so that it is in communication with the balloon fluid 132 that is positioned within the balloon interior 146 of the inflatable balloon 104. For example, in some embodiments, as shown in FIG. 1, the first electrode 158 can be positioned within the balloon interior 146. Alternatively, the first electrode 158 can be positioned in another suitable location that is in communication with the balloon fluid 132 within the balloon interior 146. For example, in certain non-exclusive alternative embodiments, the first electrode 158 can be positioned within the handle assembly 128, within and/or adjacent to the inflation conduit 140, within and/or adjacent to the inflation lumen, and/or in another suitable location.

Additionally, the second electrode 160 can be positioned at any suitable location within the catheter system 100 so that it is in communication with the blood of the patient, i.e. so that no nonconductive materials of the catheter system 100 are positioned between the second electrode 160 and the blood of the patient 109. For example, in some embodiments, as shown in FIG. 1, the second electrode 160 can be positioned on and/or adjacent to the skin 105 of the patient 109. Alternatively, the second electrode 160 can be positioned in another suitable location that is in communication with the blood of the patient 109. For example, in certain non-exclusive alternative embodiments, the second electrode 160 can be positioned inside the fluid channel within the guidewire lumen 118, on the guidewire 112, and/or in another suitable location.

It is appreciated that with the general design of the electrical analyzer assembly 142 described herein, while the first electrode 158 is in communication with the balloon fluid 132 within the balloon interior 146, during normal operation the first electrode 158 is not in communication with the blood of the patient 109 as at least the nonconductive materials of the inflatable balloon 104 are positioned therebetween. Similarly, it is further appreciated that while the second electrode 160 is in communication with the blood of the patient 109, during normal operation the second electrode 160 is not in communication with the balloon fluid 132 within the balloon interior 146 as at least the nonconductive materials of the inflatable balloon 104 are positioned therebetween.

As noted above, the impedance detector 162 is connected in electrical communication with each of the first electrode 158 and the second electrode 160. As such, the impedance detector 162 is configured to detect and thus provide real-time continuous monitoring of the impedance between the first electrode 158 and the second electrode 160. Impedance is the effective measurement of the degree a body resists the flow of electrical current, with the body's fluid and tissues acting as conductors of electrical current. It is appreciated that the impedance detector 162 can be electrically coupled to each of the first electrode 158 and the second electrode 160 via a wireless connection, or via a wired connection.

The impedance detector 162 can be positioned in any suitable location where it can be in electrical communication with the first electrode 158 and the second electrode 160. For example, in some embodiments, as shown in FIG. 1, the impedance detector 162 can be positioned substantially within the system console 123 and/or adjacent to the system controller 126. Alternatively, the impedance detector 162 can be positioned in another suitable location within the catheter system 100. For example, in certain non-exclusive alternative embodiments, the impedance detector 162 can be positioned within and/or adjacent to the handle assembly 128, inside the catheter 102, and/or in another suitable location.

As provided herein, the impedance detector 162 is configured to detect the impedance between the first electrode 158 and the second electrode 160 during operation of the catheter system 100. The impedance detector 162 can then generate a detector signal or detector output, e.g., electrical signals regarding the detected impedance, and send the detector signal or detector output to the system controller 126 and/or the circuitry 156 within the handle assembly 128 for processing. The system controller 126 can then provide appropriate information to the user or operator, e.g., via the GUI 127, as to the status of operation of the catheter system 100, e.g., the potential rupturing of the inflatable balloon 104. It is appreciated that the impedance detector 162 can be electrically connected to the system controller 126 via a wireless connection, or via a wired connection.

Under normal operating circumstances, the detected impedance would be very high, e.g., within an expected impedance range, since the first electrode 158 is insulated from the second electrode 160 by the nonconductive materials of the catheter 102. Additionally, the impedance detector 162 and/or the system controller 126 would process the detector signal to look for sudden drops in impedance between the electrodes 158, 160, which would indicate a rupture of the inflatable balloon 104, since a ruptured inflatable balloon 104 would remove the insulated barrier between the electrodes 158, 160.

Thus, in summary, if the inflatable balloon 104 ruptures, the procedure must be stopped immediately. The present invention detects this failure and provides an indicator or signal that the system controller 126 could use to lock out the energy source 124. This provides a necessary safety interlock for a potentially hazardous condition in which the energy source 124 is able to leak out of the ruptured inflatable balloon 104. Moreover, the signal could be used to indicate to the user or operator, e.g., via the GUI 127, to halt the procedure and remove the inflatable balloon 104 from the patient 109 under treatment.

Figure 2:
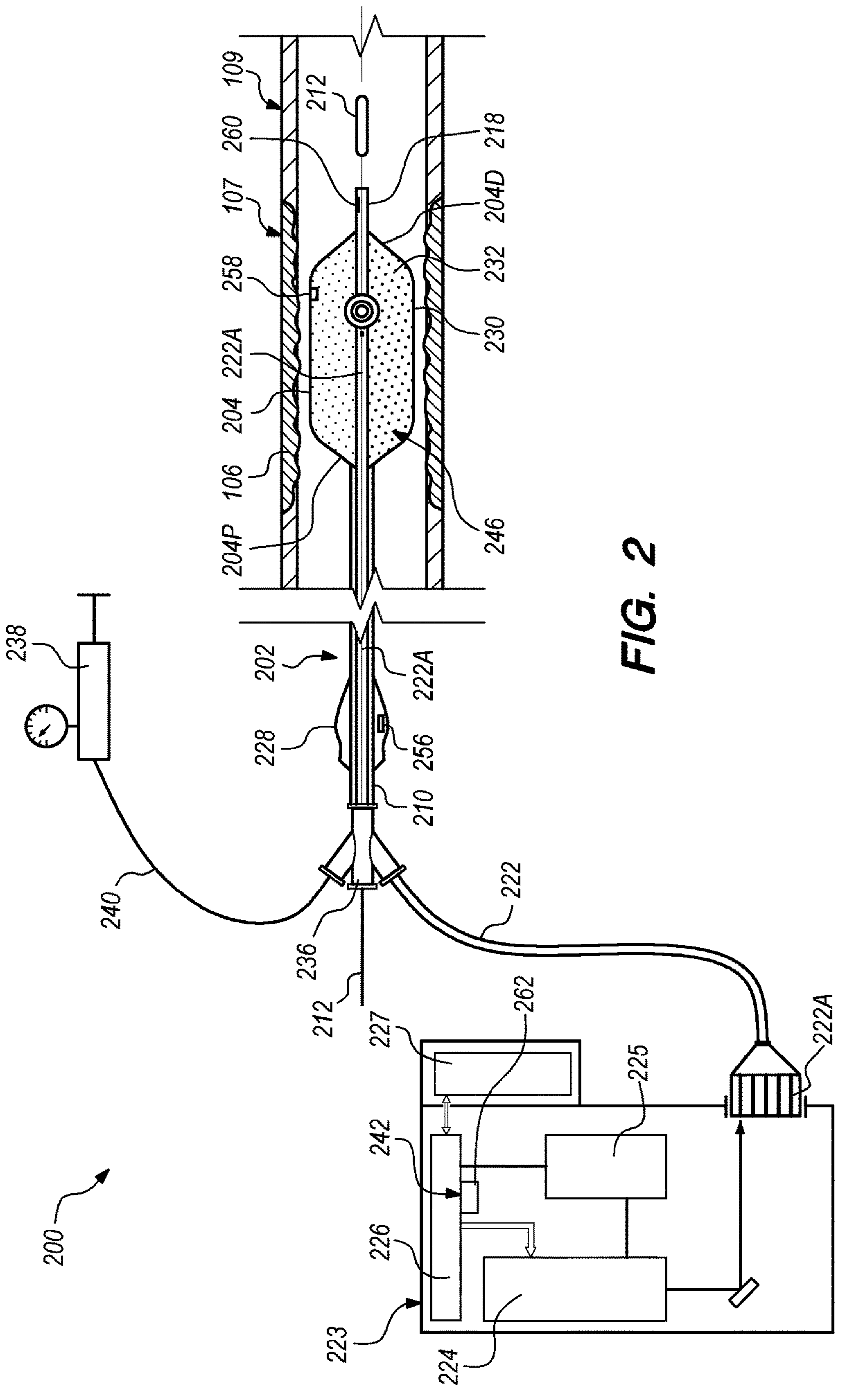
FIG. 2 is a schematic cross-sectional view of another embodiment of the catheter system including another embodiment of the electrical analyzer assembly.

FIG. 2 is a schematic cross-sectional view of another embodiment of the catheter system 200 including another embodiment of the electrical analyzer assembly 242. The design of the catheter system 200 is substantially similar to the embodiment illustrated and described herein above. In particular, in the embodiment shown in FIG. 2, the catheter system 200 can again include a catheter 202 including a catheter shaft 210, an inflatable balloon 204 having a balloon wall 230 that defines a balloon interior 246, a balloon proximal end 204P, and a balloon distal end 204D, a balloon fluid 232 that is retained substantially within the balloon interior 246, a guidewire 212, and a guidewire lumen 218 that extends into the balloon interior 246; an energy guide bundle 222 including one or more energy guides 222A; a source manifold 236; a fluid pump 238; a system console 223 including one or more of an energy source 224, a power source 225, a system controller 226, and a GUI 227; a handle assembly 228; and the electrical analyzer assembly 242. Alternatively, in other embodiments, the catheter system 200 can include more components or fewer components than what is specifically illustrated and described herein.

The catheter 202, including the catheter shaft 210, the inflatable balloon 204, the guidewire 212, and the guidewire lumen 218, is generally similar in design and operation to what has been described in detail herein above. Thus, such components will not be described in detail again in relation to the embodiment shown in FIG. 2.

As above, the inflatable balloon 204 is selectively movable between a collapsed configuration suitable for advancing the catheter 202 through a patient's vasculature, and an expanded configuration suitable for anchoring the catheter 202 in position relative to the treatment site 106. In some embodiments, the balloon proximal end 204P can be coupled to the catheter shaft 210, and the balloon distal end 204D can be coupled to the guidewire lumen 218. Additionally, the inflatable balloon 204 can be inflated with the balloon fluid 232, e.g., from the fluid pump 238, that is directed into the balloon interior 246 of the inflatable balloon 204 via the inflation conduit 240.

Additionally, the energy guide bundle 222 including the one or more energy guides 222A, and the system console 223 including one or more of the energy source 224, the power source 225, the system controller 226, and the GUI 227, are generally similar in design and operation to what has been described in detail herein above. Accordingly, such components will not be described in detail again in relation to the embodiment shown in FIG. 2.

Further, as above, the handle assembly 228 is handled and used by the user or operator to operate, position and control the catheter 202. Additionally, as shown in the embodiment illustrated in FIG. 2, the handle assembly 228 can again include circuitry 256 that can form a portion of the system controller 226. Alternatively, the handle assembly 228 can be configured without the circuitry 256.

As with the previous embodiment, the electrical analyzer assembly 242 is again configured to monitor the performance, reliability and safety of the catheter system 200. Additionally, the design of the electrical analyzer assembly 242 can be somewhat similar to what was illustrated and described herein above in relation to the embodiment shown in FIG. 1. For example, the electrical analyzer assembly 242 can again include a first electrode 258, a second electrode 260, and an impedance detector 262 that is connected in electrical communication with the first electrode 258 and the second electrode 260 in order to effectively measure and/or detect the impedance between the first electrode 258 and the second electrode 260.

However, in the embodiment shown in FIG. 2, one or more of the first electrode 258, the second electrode 260 and the impedance detector 262 can be positioned in a different manner than in the previous embodiment. More particularly, as shown in FIG. 2, in this embodiment, the first electrode 258 is again positioned within the balloon interior 246, and the impedance detector 262 is again positioned adjacent to and/or in electrical communication with the system controller 226, but the second electrode 260 is now positioned inside the fluid channel within the guidewire lumen 218.

It is appreciated that with such design, during normal operation, the first electrode 258 is still in communication with the balloon fluid 232 within the balloon interior 246, but not in communication with the blood of the patient 109; and the second electrode 260 is still in communication with the blood of the patient 109, but not in communication with the balloon fluid 232 within the balloon interior 246. Additionally, it is further appreciated that with such design, the impedance detector 262, in conjunction with the system controller 226 and/or the circuitry 256 in the handle assembly 228, is still configured to look for sudden drops in impedance between the electrodes 258, 260 as an indication of damage to and/or rupture of the inflatable balloon 204, which would necessitate that the procedure be immediately stopped and the catheter 202 removed from the patient 109.

Figure 3:
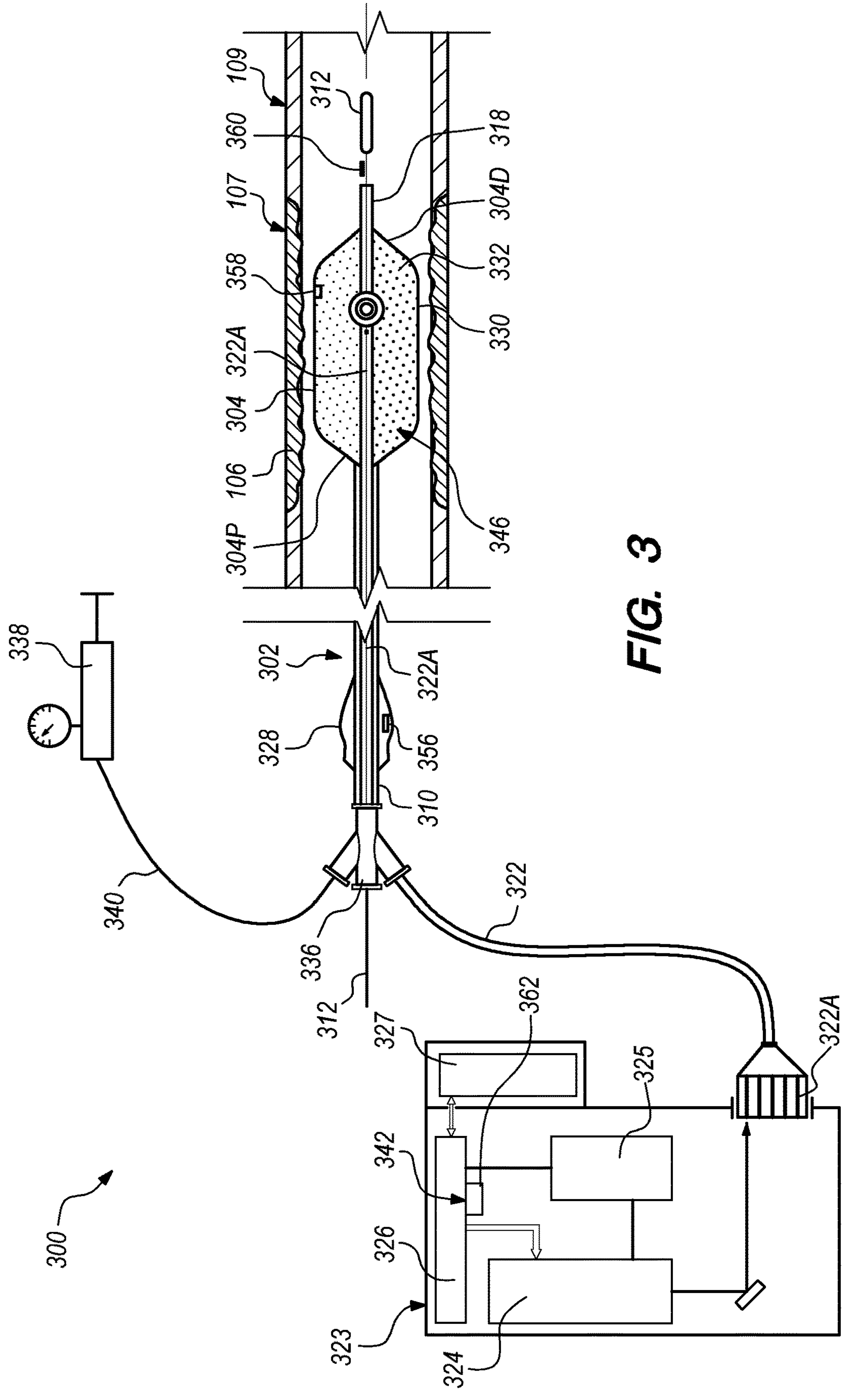
FIG. 3 is a schematic cross-sectional view of still another embodiment of the catheter system including still another embodiment of the electrical analyzer assembly.

FIG. 3 is a schematic cross-sectional view of still another embodiment of the catheter system 300 including still another embodiment of the electrical analyzer assembly 342. The design of the catheter system 300 is substantially similar to the embodiments illustrated and described herein above. In particular, in the embodiment shown in FIG. 3, the catheter system 300 can again include a catheter 302 including a catheter shaft 310, an inflatable balloon 304 having a balloon wall 330 that defines a balloon interior 346, a balloon proximal end 304P, and a balloon distal end 304D, a balloon fluid 332 that is retained substantially within the balloon interior 346, a guidewire 312, and a guidewire lumen 318 that extends into the balloon interior 346; an energy guide bundle 322 including one or more energy guides 322A; a source manifold 336; a fluid pump 338; a system console 323 including one or more of an energy source 324, a power source 325, a system controller 326, and a GUI 327; a handle assembly 328; and the electrical analyzer assembly 342. Alternatively, in other embodiments, the catheter system 300 can include more components or fewer components than what is specifically illustrated and described herein.

The catheter 302, including the catheter shaft 310, the inflatable balloon 304, the guidewire 312, and the guidewire lumen 318, is generally similar in design and operation to what has been described in detail herein above. Thus, such components will not be described in detail again in relation to the embodiment shown in FIG. 3.

As above, the inflatable balloon 304 is selectively movable between a collapsed configuration suitable for advancing the catheter 302 through a patient's vasculature, and an expanded configuration suitable for anchoring the catheter 302 in position relative to the treatment site 106. In some embodiments, the balloon proximal end 304P can be coupled to the catheter shaft 310, and the balloon distal end 304D can be coupled to the guidewire lumen 318. Additionally, the inflatable balloon 304 can be inflated with the balloon fluid 332, e.g., from the fluid pump 338, that is directed into the balloon interior 346 of the inflatable balloon 304 via the inflation conduit 340.

Additionally, the energy guide bundle 322 including the one or more energy guides 322A, and the system console 323 including one or more of the energy source 324, the power source 325, the system controller 326, and the GUI 327, are generally similar in design and operation to what has been described in detail herein above. Accordingly, such components will not be described in detail again in relation to the embodiment shown in FIG. 3.

Further, as above, the handle assembly 328 is handled and used by the user or operator to operate, position and control the catheter 302. Additionally, as shown in the embodiment illustrated in FIG. 3, the handle assembly 328 can again include circuitry 356 that can form a portion of the system controller 326. Alternatively, the handle assembly 328 can be configured without the circuitry 356.

As with the previous embodiments, the electrical analyzer assembly 342 is again configured to monitor the performance, reliability and safety of the catheter system 300. Additionally, the design of the electrical analyzer assembly 342 can be somewhat similar to what was illustrated and described herein above in relation to the previous embodiments. For example, the electrical analyzer assembly 342 can again include a first electrode 358, a second electrode 360, and an impedance detector 362 that is connected in electrical communication with the first electrode 358 and the second electrode 360 in order to effectively measure and/or detect the impedance between the first electrode 358 and the second electrode 360.

However, in the embodiment shown in FIG. 3, one or more of the first electrode 358, the second electrode 360 and the impedance detector 362 can be positioned in a different manner than in the previous embodiments. More particularly, as shown in FIG. 3, in this embodiment, the first electrode 358 is again positioned within the balloon interior 346, and the impedance detector 362 is again positioned adjacent to and/or in electrical communication with the system controller 326, but the second electrode 360 is now positioned on and/or adjacent to the guidewire 312.

It is appreciated that with such design, during normal operation, the first electrode 358 is still in communication with the balloon fluid 332 within the balloon interior 346, but not in communication with the blood of the patient 109; and the second electrode 360 is still in communication with the blood of the patient 109, but not in communication with the balloon fluid 332 within the balloon interior 346. Additionally, it is further appreciated that with such design, the impedance detector 362, in conjunction with the system controller 326 and/or the circuitry 356 in the handle assembly 328, is still configured to look for sudden drops in impedance between the electrodes 358, 360 as an indication of damage to and/or rupture of the inflatable balloon 304, which would necessitate that the procedure be immediately stopped and the catheter 302 be removed from the patient 109.

Figure 4:
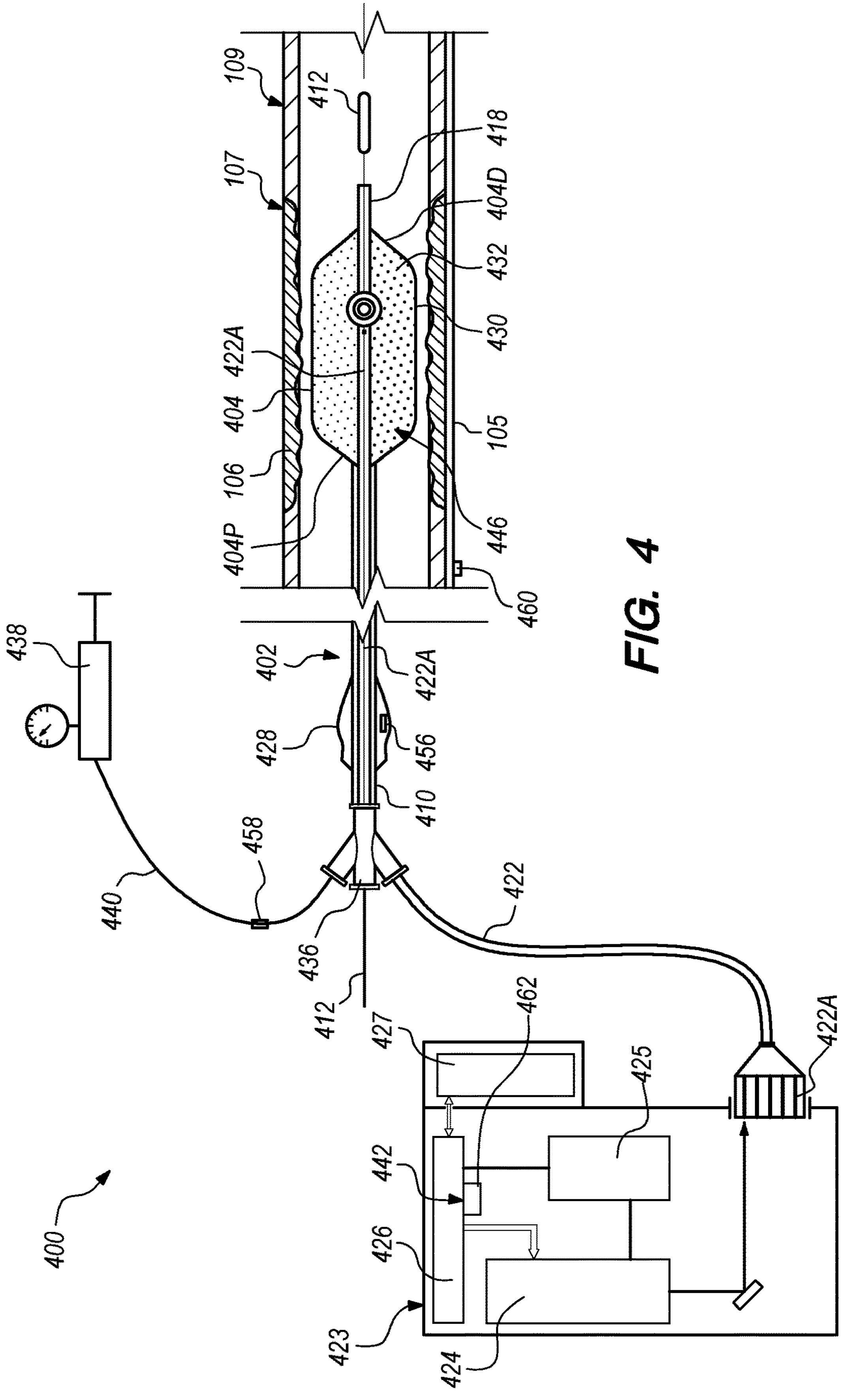
FIG. 4 is a schematic cross-sectional view of another embodiment of the catheter system including another embodiment of the electrical analyzer assembly.

FIG. 4 is a schematic cross-sectional view of another embodiment of the catheter system 400 including another embodiment of the electrical analyzer assembly 442. The design of the catheter system 400 is substantially similar to the embodiments illustrated and described herein above. In particular, in the embodiment shown in FIG. 4, the catheter system 400 can again include a catheter 402 including a catheter shaft 410, an inflatable balloon 404 having a balloon wall 430 that defines a balloon interior 446, a balloon proximal end 404P, and a balloon distal end 404D, a balloon fluid 432 that is retained substantially within the balloon interior 446, a guidewire 412, and a guidewire lumen 418 that extends into the balloon interior 446; an energy guide bundle 422 including one or more energy guides 422A; a source manifold 436; a fluid pump 438; a system console 423 including one or more of an energy source 424, a power source 425, a system controller 426, and a GUI 427; a handle assembly 428; and the electrical analyzer assembly 442. Alternatively, in other embodiments, the catheter system 400 can include more components or fewer components than what is specifically illustrated and described herein.

The catheter 402, including the catheter shaft 410, the inflatable balloon 404, the guidewire 412, and the guidewire lumen 418, is generally similar in design and operation to what has been described in detail herein above. Thus, such components will not be described in detail again in relation to the embodiment shown in FIG. 4.

As above, the inflatable balloon 404 is selectively movable between a collapsed configuration suitable for advancing the catheter 402 through a patient's vasculature, and an expanded configuration suitable for anchoring the catheter 402 in position relative to the treatment site 106. In some embodiments, the balloon proximal end 404P can be coupled to the catheter shaft 410, and the balloon distal end 404D can be coupled to the guidewire lumen 418. Additionally, the inflatable balloon 404 can be inflated with the balloon fluid 432, e.g., from the fluid pump 438, that is directed into the balloon interior 446 of the inflatable balloon 404 via the inflation conduit 440.

Additionally, the energy guide bundle 422 including the one or more energy guides 422A, and the system console 423 including one or more of the energy source 424, the power source 425, the system controller 426, and the GUI 427, are generally similar in design and operation to what has been described in detail herein above. Accordingly, such components will not be described in detail again in relation to the embodiment shown in FIG. 4.

Further, as above, the handle assembly 428 is handled and used by the user or operator to operate, position and control the catheter 402. Additionally, as shown in the embodiment illustrated in FIG. 4, the handle assembly 428 can again include circuitry 456 that can form a portion of the system controller 426. Alternatively, the handle assembly 428 can be configured without the circuitry 456.

As with the previous embodiments, the electrical analyzer assembly 442 is again configured to monitor the performance, reliability and safety of the catheter system 400. Additionally, the design of the electrical analyzer assembly 442 can be somewhat similar to what was illustrated and described herein above in relation to the previous embodiments. For example, the electrical analyzer assembly 442 can again include a first electrode 458, a second electrode 460, and an impedance detector 462 that is connected in electrical communication with the first electrode 458 and the second electrode 460 in order to effectively measure and/or detect the impedance between the first electrode 458 and the second electrode 460.

However, in the embodiment shown in FIG. 4, one or more of the first electrode 458, the second electrode 460 and the impedance detector 462 can be positioned in a different manner than in the previous embodiments. More particularly, as shown in FIG. 4, in this embodiment, the second electrode 460 is again positioned on and/or adjacent to the skin 105 of the patient 109 (as in the embodiment shown in FIG. 1), and the impedance detector 462 is again positioned adjacent to and/or in electrical communication with the system controller 426, but the first electrode 458 is now positioned within and/or adjacent to the inflation conduit 440 through which balloon fluid 432 is directed into the balloon interior 446 of the inflatable balloon 404.

It is appreciated that with such design, during normal operation, the first electrode 458 is still in communication with the balloon fluid 432 within the balloon interior 446, but not in communication with the blood of the patient 109; and the second electrode 460 is still in communication with the blood of the patient 109, but not in communication with the balloon fluid 432 within the balloon interior 446. Additionally, it is further appreciated that with such design, the impedance detector 462, in conjunction with the system controller 426 and/or the circuitry 456 in the handle assembly 428, is still configured to look for sudden drops in impedance between the electrodes 458, 460 as an indication of damage to and/or rupture of the inflatable balloon 404, which would necessitate that the procedure be immediately stopped and the catheter 402 be removed from the patient 109.

Figure 5:
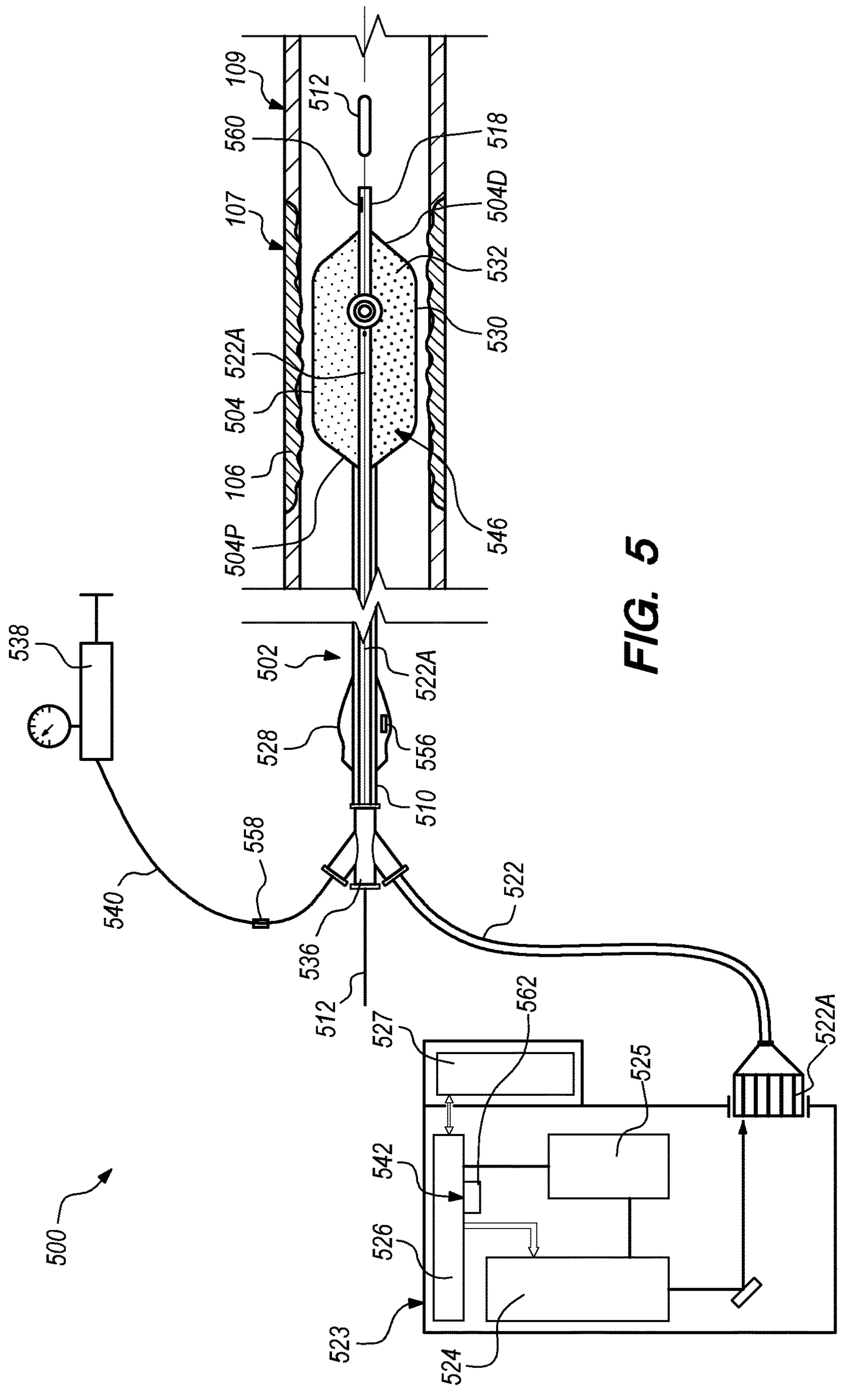
FIG. 5 is a schematic cross-sectional view of yet another embodiment of the catheter system including yet another embodiment of the electrical analyzer assembly.

FIG. 5 is a schematic cross-sectional view of yet another embodiment of the catheter system 500 including yet another embodiment of the electrical analyzer assembly 542. The design of the catheter system 500 is substantially similar to the embodiments illustrated and described herein above. In particular, in the embodiment shown in FIG. 5, the catheter system 500 can again include a catheter 502 including a catheter shaft 510, an inflatable balloon 504 having a balloon wall 530 that defines a balloon interior 546, a balloon proximal end 504P, and a balloon distal end 504D, a balloon fluid 532 that is retained substantially within the balloon interior 546, a guidewire 512, and a guidewire lumen 518 that extends into the balloon interior 546; an energy guide bundle 522 including one or more energy guides 522A; a source manifold 536; a fluid pump 538; a system console 523 including one or more of an energy source 524, a power source 525, a system controller 526, and a GUI 527; a handle assembly 528; and the electrical analyzer assembly 542. Alternatively, in other embodiments, the catheter system 500 can include more components or fewer components than what is specifically illustrated and described herein.

The catheter 502, including the catheter shaft 510, the inflatable balloon 504, the guidewire 512, and the guidewire lumen 518, is generally similar in design and operation to what has been described in detail herein above. Thus, such components will not be described in detail again in relation to the embodiment shown in FIG. 5.

As above, the inflatable balloon 504 is selectively movable between a collapsed configuration suitable for advancing the catheter 502 through a patient's vasculature, and an expanded configuration suitable for anchoring the catheter 502 in position relative to the treatment site 106. In some embodiments, the balloon proximal end 504P can be coupled to the catheter shaft 510, and the balloon distal end 504D can be coupled to the guidewire lumen 518. Additionally, the inflatable balloon 504 can be inflated with the balloon fluid 532, e.g., from the fluid pump 538, that is directed into the balloon interior 546 of the inflatable balloon 504 via the inflation conduit 540.

Additionally, the energy guide bundle 522 including the one or more energy guides 522A, and the system console 523 including one or more of the energy source 524, the power source 525, the system controller 526, and the GUI 527, are generally similar in design and operation to what has been described in detail herein above. Accordingly, such components will not be described in detail again in relation to the embodiment shown in FIG. 5.

Further, as above, the handle assembly 528 is handled and used by the user or operator to operate, position and control the catheter 502. Additionally, as shown in the embodiment illustrated in FIG. 5, the handle assembly 528 can again include circuitry 556 that can form a portion of the system controller 526. Alternatively, the handle assembly 528 can be configured without the circuitry 556.

As with the previous embodiments, the electrical analyzer assembly 542 is again configured to monitor the performance, reliability and safety of the catheter system 500. Additionally, the design of the electrical analyzer assembly 542 can be somewhat similar to what was illustrated and described herein above in relation to the previous embodiments. For example, the electrical analyzer assembly 542 can again include a first electrode 558, a second electrode 560, and an impedance detector 562 that is connected in electrical communication with the first electrode 558 and the second electrode 560 in order to effectively measure and/or detect the impedance between the first electrode 558 and the second electrode 560.

However, in the embodiment shown in FIG. 5, one or more of the first electrode 558, the second electrode 560 and the impedance detector 562 can be positioned in a different manner than in the previous embodiments. More particularly, as shown in FIG. 5, in this embodiment, the first electrode 558 is again positioned within and/or adjacent to the inflation conduit 540 through which balloon fluid 532 is directed into the balloon interior 546 of the inflatable balloon 504 (as in FIG. 4), the second electrode 560 is again positioned within and/or adjacent to the guidewire lumen 518 (as in the embodiment shown in FIG. 2), and the impedance detector 562 is again positioned adjacent to and/or in electrical communication with the system controller 526.

It is appreciated that with such design, during normal operation, the first electrode 558 is still in communication with the balloon fluid 532 within the balloon interior 546, but not in communication with the blood of the patient 109; and the second electrode 560 is still in communication with the blood of the patient 109, but not in communication with the balloon fluid 532 within the balloon interior 546. Additionally, it is further appreciated that with such design, the impedance detector 562, in conjunction with the system controller 526 and/or the circuitry 556 in the handle assembly 528, is still configured to look for sudden drops in impedance between the electrodes 558, 560 as an indication of damage to and/or rupture of the inflatable balloon 504, which would necessitate that the procedure be immediately stopped and the catheter 502 be removed from the patient 109.

Figure 6:
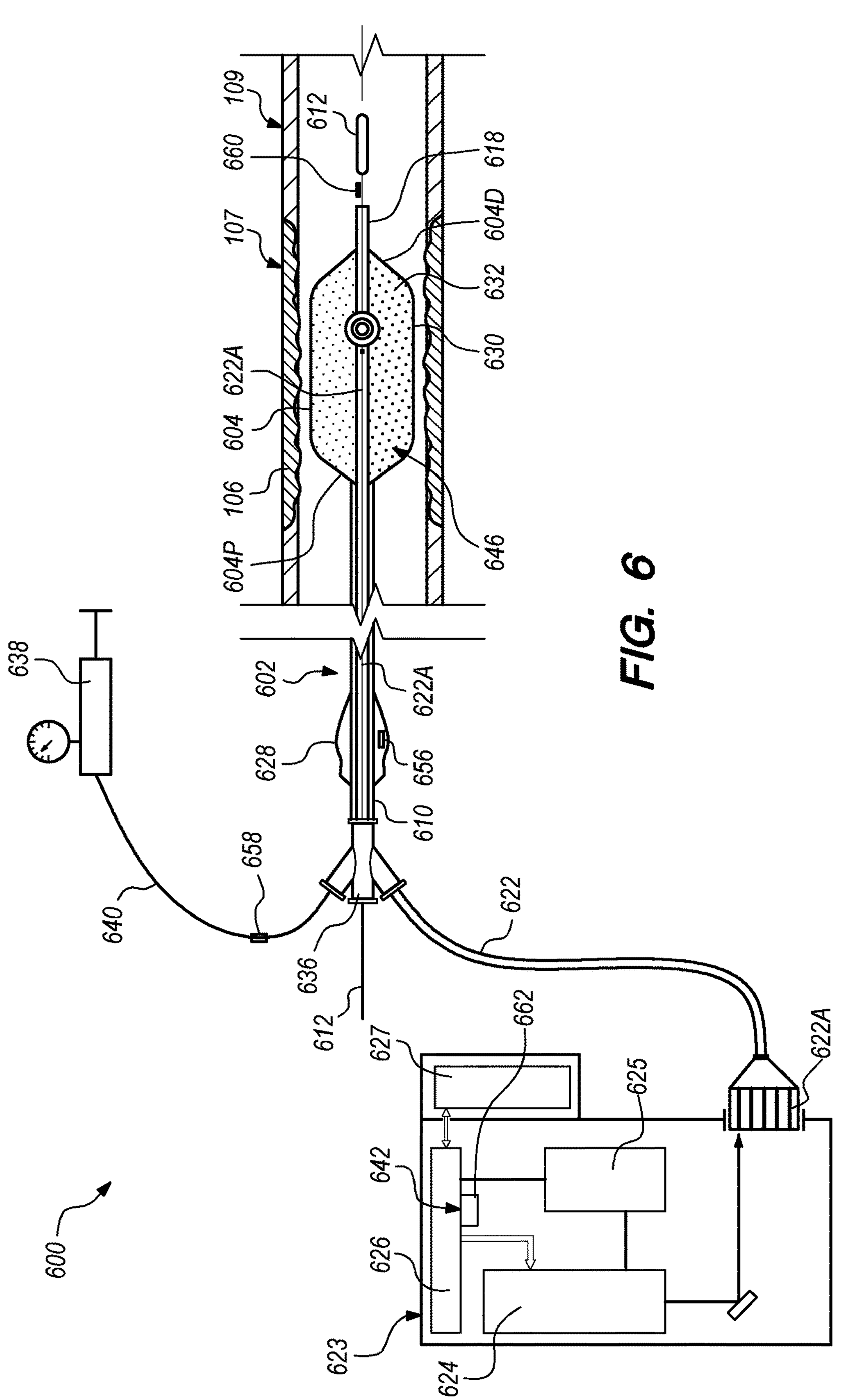
FIG. 6 is a schematic cross-sectional view of still yet another embodiment of the catheter system including still yet another embodiment of the electrical analyzer assembly.

FIG. 6 is a schematic cross-sectional view of still yet another embodiment of the catheter system 600 including still yet another embodiment of the electrical analyzer assembly 642. The design of the catheter system 600 is substantially similar to the embodiments illustrated and described herein above. In particular, in the embodiment shown in FIG. 6, the catheter system 600 can again include a catheter 602 including a catheter shaft 610, an inflatable balloon 604 having a balloon wall 630 that defines a balloon interior 646, a balloon proximal end 604P, and a balloon distal end 604D, a balloon fluid 632 that is retained substantially within the balloon interior 646, a guidewire 612, and a guidewire lumen 618 that extends into the balloon interior 646; an energy guide bundle 622 including one or more energy guides 622A; a source manifold 636; a fluid pump 638; a system console 623 including one or more of an energy source 624, a power source 625, a system controller 626, and a GUI 627; a handle assembly 628; and the electrical analyzer assembly 642. Alternatively, in other embodiments, the catheter system 600 can include more components or fewer components than what is specifically illustrated and described herein.

The catheter 602, including the catheter shaft 610, the inflatable balloon 604, the guidewire 612, and the guidewire lumen 618, is generally similar in design and operation to what has been described in detail herein above. Thus, such components will not be described in detail again in relation to the embodiment shown in FIG. 6.

As above, the inflatable balloon 604 is selectively movable between a collapsed configuration suitable for advancing the catheter 602 through a patient's vasculature, and an expanded configuration suitable for anchoring the catheter 602 in position relative to the treatment site 106. In some embodiments, the balloon proximal end 604P can be coupled to the catheter shaft 610, and the balloon distal end 604D can be coupled to the guidewire lumen 618. Additionally, the inflatable balloon 604 can be inflated with the balloon fluid 632, e.g., from the fluid pump 638, that is directed into the balloon interior 646 of the inflatable balloon 604 via the inflation conduit 640.

Additionally, the energy guide bundle 622 including the one or more energy guides 622A, and the system console 623 including one or more of the energy source 624, the power source 625, the system controller 626, and the GUI 627, are generally similar in design and operation to what has been described in detail herein above. Accordingly, such components will not be described in detail again in relation to the embodiment shown in FIG. 6.

Further, as above, the handle assembly 628 is handled and used by the user or operator to operate, position and control the catheter 602. Additionally, as shown in the embodiment illustrated in FIG. 6, the handle assembly 628 can again include circuitry 656 that can form a portion of the system controller 626. Alternatively, the handle assembly 628 can be configured without the circuitry 656.

As with the previous embodiments, the electrical analyzer assembly 642 is again configured to monitor the performance, reliability and safety of the catheter system 600. Additionally, the design of the electrical analyzer assembly 642 can be somewhat similar to what was illustrated and described herein above in relation to the previous embodiments. For example, the electrical analyzer assembly 642 can again include a first electrode 658, a second electrode 660, and an impedance detector 662 that is connected in electrical communication with the first electrode 658 and the second electrode 660 in order to effectively measure and/or detect the impedance between the first electrode 658 and the second electrode 660.

However, in the embodiment shown in FIG. 6, one or more of the first electrode 658, the second electrode 660 and the impedance detector 662 can be positioned in a different manner than in the previous embodiments. More particularly, as shown in FIG. 6, in this embodiment, the first electrode 658 is again positioned within and/or adjacent to the inflation conduit 640 through which balloon fluid 632 is directed into the balloon interior 646 of the inflatable balloon 604 (as in FIG. 4), the second electrode 660 is again positioned on and/or adjacent to the guidewire 612 (as in the embodiment shown in FIG. 3), and the impedance detector 662 is again positioned adjacent to and/or in electrical communication with the system controller 626.

It is appreciated that with such design, during normal operation, the first electrode 658 is still in communication with the balloon fluid 632 within the balloon interior 646, but not in communication with the blood of the patient 109; and the second electrode 660 is still in communication with the blood of the patient 109, but not in communication with the balloon fluid 632 within the balloon interior 646. Additionally, it is further appreciated that with such design, the impedance detector 662, in conjunction with the system controller 626 and/or the circuitry 656 in the handle assembly 628, is still configured to look for sudden drops in impedance between the electrodes 658, 660 as an indication of damage to and/or rupture of the inflatable balloon 604, which would necessitate that the procedure be immediately stopped and the catheter 602 be removed from the patient 109.

As noted above, the electrical analyzer assembly of the present invention addresses several important challenges with the performance, reliability and safety of an intravascular lithotripsy catheter, in particular one that utilizes an energy source, e.g., a light source such as a laser source, to create a localized plasma which in turn induces a high energy bubble in the balloon fluid within the balloon interior of the balloon. For example, as noted above, issues that are addressed by the present invention include, but are not limited to: 1) electrical detection of normal operation and/or balloon condition used within the catheter system, and 2) electrical detection of a failure of the balloon, e.g., damage to and/or rupture of the balloon, during use of the catheter system, which would necessitate shutting down of the catheter system and removal of the catheter from the body of the patient.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A method for treating a treatment site within or adjacent to a vessel wall or heart valve within a body of a patient, the method comprising steps of:

generating energy with an energy source;

positioning a balloon substantially adjacent to the treatment site, the balloon having a balloon wall that defines a balloon interior that receives a balloon fluid;

receiving energy from the energy source with an energy guide;

guiding the energy with the energy guide into the balloon interior;

monitoring a condition of the balloon with an electrical analyzer assembly while energy is being guided into the balloon interior, the electrical analyzer assembly including (i) a first electrode, (ii) a second electrode that is in fluid communication with blood of the patient, and (iii) an impedance detector that is electrically coupled to the first electrode and the second electrode; and detecting an impedance between the first electrode and the second electrode with the impedance detector.

2. The method of claim 1 wherein the step of monitoring includes analyzing an electrical signal with the electrical analyzer assembly, and determining the condition of the balloon with the electrical analyzer assembly based at least in part on the electrical signal.

3. The method of claim 1 wherein the step of monitoring includes analyzing an electrical signal with the electrical analyzer assembly, and determining with the electrical analyzer assembly whether a rupture of the balloon has occurred based at least in part on the electrical signal.

4. The method of claim 1 wherein when a rupture in the balloon has not occurred, the step of monitoring includes steps of positioning the first electrode to be in fluid communication with the balloon fluid in the balloon interior, and positioning the second electrode to be not in fluid communication with the balloon fluid in the balloon interior.

5. The method of claim 1 further comprising a step of generating a detector signal with the impedance detector based at least in part on the detected impedance between the first electrode and the second electrode.

6. The method of claim 5 further comprising steps of electrically coupling a system controller to the impedance detector; receiving the detector signal from the impedance detector with the system controller; and determining the condition of the balloon with the system controller based at least in part on the detector signal.

7. The method of claim 6 wherein the step of electrically coupling includes electrically coupling the system controller to the impedance detector via a wired connection.

8. The method of claim 6 wherein the step of electrically coupling includes electrically coupling the system controller to the acoustic sensor via a wireless connection.

9. The method of claim 6 further comprising a step of recognizing a normal condition of the balloon with the system controller based at least in part on the detector signal.

10. The method of claim 6 further comprising a step of recognizing a potential rupture of the balloon with the system controller based at least in part on the detector signal.

11. The method of claim 10 further comprising a step of automatically shutting down operation of the catheter system with the system controller upon recognition of the potential rupture of the balloon.

12. The method of claim 1 wherein the step of monitoring includes positioning the first electrode within the balloon interior.

13. The method of claim 1 further comprising a step of directing the balloon fluid into the balloon interior via an inflation conduit; and wherein the step of monitoring includes positioning the first electrode within an inflation conduit.

14. The method of claim 1 further comprising a step of guiding positioning of the balloon substantially adjacent to the treatment site with a guidewire; and wherein the step of monitoring includes positioning the second electrode substantially adjacent to the guidewire.

15. The method of claim 1 further comprising steps of guiding positioning of the balloon substantially adjacent to the treatment site with a guidewire, and moving a guidewire lumen over the guidewire; and wherein the step of monitoring includes positioning the second electrode within the guidewire lumen.

16. The method of claim 1 wherein the step of generating includes the energy source being a laser source that provides pulses of laser energy; and wherein the step of receiving includes the energy guide including an optical fiber.

17. A method for treating a treatment site within or adjacent to a vessel wall or heart valve within a body of a patient, the method comprising steps of:

generating energy with an energy source;

positioning a balloon substantially adjacent to the treatment site, the balloon having a balloon wall that defines a balloon interior that receives a balloon fluid;

directing the balloon fluid into the balloon interior through an inflation conduit;

receiving energy from the energy source with an energy guide;

guiding the energy with the energy guide into the balloon interior;

monitoring a condition of the balloon with an electrical analyzer assembly while energy is being guided into the balloon interior, the electrical analyzer assembly including (i) a first electrode that is positioned within the inflation conduit, (ii) a second electrode, and (iii) an impedance detector that is electrically coupled to the first electrode and the second electrode; and detecting an impedance between the first electrode and the second electrode with the impedance detector.

18. The method of claim 17 wherein the step of monitoring includes positioning the second electrode on skin of the patient.

19. A method for treating a treatment site within or adjacent to a vessel wall or heart valve within a body of a patient, the method comprising steps of:

generating energy with an energy source;

positioning a balloon substantially adjacent to the treatment site, the balloon having a balloon wall that defines a balloon interior that receives a balloon fluid;

guiding positioning of the balloon substantially adjacent to the treatment site with a guidewire;

receiving energy from the energy source with an energy guide;

guiding the energy with the energy guide into the balloon interior;

monitoring a condition of the balloon with an electrical analyzer assembly while energy is being guided into the balloon interior, the electrical analyzer assembly including (i) a first electrode, (ii) a second electrode that is positioned substantially adjacent to the guidewire, and (iii) an impedance detector that is electrically coupled to the first electrode and the second electrode; and detecting an impedance between the first electrode and the second electrode with the impedance detector.

20. The method of claim 19 wherein the step of monitoring includes positioning the first electrode in fluid communication with the balloon fluid.

* * * * *